(12) United States Patent
Kasahara

(10) Patent No.: US 7,850,687 B2
(45) Date of Patent: *Dec. 14, 2010

(54) INSTRUMENT FOR CUTTING LIVING TISSUE

(75) Inventor: Hideyuki Kasahara, Hachioji (JP)

(73) Assignee: Olympus Corporation, Tokyo (JP)

( * ) Notice: Subject to any disclaimer, the term of this patent is extended or adjusted under 35 U.S.C. 154(b) by 1227 days.

This patent is subject to a terminal disclaimer.

(21) Appl. No.: 11/418,533

(22) Filed: May 3, 2006

(65) Prior Publication Data

US 2006/0206112 A1 Sep. 14, 2006

Related U.S. Application Data

(63) Continuation of application No. PCT/JP2005/011238, filed on Jun. 20, 2005.

(30) Foreign Application Priority Data

| Jun. 18, 2004 | (JP) | ............................. 2004-181523 |
| Oct. 18, 2004 | (JP) | ............................. 2004-303414 |

(51) Int. Cl.
 *A61B 18/18* (2006.01)
(52) U.S. Cl. ...................................... 606/45
(58) Field of Classification Search .................. 606/41, 606/45–50
See application file for complete search history.

(56) References Cited

U.S. PATENT DOCUMENTS

| 3,970,088 | A | | 7/1976 | Morrison |
| 5,078,716 | A | * | 1/1992 | Doll ............................ 606/47 |
| 5,151,102 | A | * | 9/1992 | Kamiyama et al. ............ 606/51 |
| 5,697,281 | A | | 12/1997 | Eggers et al. |
| 5,891,141 | A | * | 4/1999 | Rydell ......................... 606/45 |
| 6,022,313 | A | * | 2/2000 | Ginn et al. .................... 600/114 |
| 6,056,747 | A | * | 5/2000 | Saadat et al. ................... 606/50 |
| 6,165,175 | A | * | 12/2000 | Wampler et al. .............. 606/48 |
| 6,193,653 | B1 | * | 2/2001 | Evans et al. .................. 600/210 |
| 6,443,970 | B1 | * | 9/2002 | Schulze et al. .............. 606/171 |
| 6,558,385 | B1 | * | 5/2003 | McClurken et al. ........... 606/50 |
| 7,316,683 | B2 | * | 1/2008 | Kasahara et al. .............. 606/45 |
| 2002/0049440 | A1 | * | 4/2002 | Svejkovsky et al. ........... 606/46 |

(Continued)

FOREIGN PATENT DOCUMENTS

EP    1 323 392 A1    7/2003

(Continued)

*Primary Examiner*—Michael Peffley
*Assistant Examiner*—Samantha Good
(74) *Attorney, Agent, or Firm*—Scully, Scott, Murphy & Presser, P.C.

(57) ABSTRACT

An instrument for cutting a living tissue is provided to increase heat resistance to heat generated in an operation of cutting the living tissue and to ensure by stanch the blood of the tissue to be cut. The instrument for cutting a living tissue 41 includes a body part 422 having a distal end and a proximal end and on which a groove is formed through, a tissue holding part 423 made of an electrically insulating material, a slit groove 427 formed in the part where at least a part of the tissue holding part is arranged, a first electrode 425 arranged at the proximal end side of the slit groove, and a second electrode 424 arranged at the other side opposite to the side where the first electrode of the tissue holding part is arranged.

21 Claims, 33 Drawing Sheets

U.S. PATENT DOCUMENTS

| | | | |
|---|---|---|---|
| 2003/0032953 A1* | 2/2003 | VanDusseldorp et al. | 606/41 |
| 2003/0065326 A1* | 4/2003 | Wellman et al. | 606/50 |
| 2003/0088245 A1* | 5/2003 | Woloszko et al. | 606/41 |
| 2003/0125732 A1 | 7/2003 | Goble | |
| 2003/0130654 A1* | 7/2003 | Kasahara et al. | 606/45 |
| 2007/0185481 A1* | 8/2007 | Kasahara et al. | 606/37 |

FOREIGN PATENT DOCUMENTS

| | | |
|---|---|---|
| JP | 10-510745 | 10/1998 |
| JP | 2003-199765 | 7/2003 |
| JP | 2004-008241 | 1/2004 |
| JP | 2005-512726 | 5/2005 |
| WO | WO 96/39914 | 12/1996 |
| WO | WO 03/055402 A1 | 7/2003 |

\* cited by examiner

INSTRUMENT FOR CUTTING LIVING TISSUE

CROSS REFERENCES TO RELATED APPLICATIONS

This application is a continuation application of PCT/JP 2005/011238 filed on Jun. 20, 2005 and claims benefit of Japanese Patent Applications No. 2004-181523 filed in Japan on Jun. 18, 2004 and No. 2004-303414 filed in Japan on Oct. 18, 2004, the entire contents of which are incorporated herein by reference.

BACKGROUND OF THE INVENTION

1. Field of the Invention

The present invention relates to a living tissue cutting instrument which pulls a subcutaneous vessel under endoscopic observation and samples the pulled subcutaneous vessel.

2. Description of the Related Art

In recent years, in a Coronary Artery Bypass Grafting, as the blood vessel for bypassing, a blood vessel in inferior limb, for example, a great saphenous vein, of a patient himself/herself is often used. Living tissue harvesting apparatuses for harvesting the blood vessel of the inferior limb under endoscopic observation have been proposed, for example, in Japanese Unexamined Patent Application Publication No. 2004-008241.

The living tissue harvesting apparatus is composed of instruments such as a dissector, harvester, or the like. An endoscope can be inserted into the dissector and harvester, and the operator can sample the blood vessel while watching the endoscopic image. The dissector is inserted from a trocar which is a guiding tube set on an incision in the neighbor below the patient's knee, by being inserted through the entire length of the blood vessel to be sampled, gradually dissects the blood vessel and the peripheral tissues. The harvester is an instrument having a bipolar cutter used for electrically cutting a branch of the blood vessel dissected from the peripheral tissues by the dissector.

The bipolar cutter has a groove formed at the distal-end part and a pair of electrodes is provided such that the groove is held from the upper side and the lower side. If the bipolar cutter is moved forward, the branch enters into the groove of the distal-end part, then, the branch is cut with the blood being stanched by discharge of electricity from the two electrodes.

SUMMARY OF THE INVENTION

It is an object of the present invention to provide an instrument for cutting a living tissue comprising: a body part having a distal end and a proximal end and on which a groove is formed from the distal end toward the proximal end side, a tissue holding part made of an electrically insulating material being at least partially arranged in the groove; a slit groove formed in the part where at least a part of the tissue holding part is arranged toward the proximal end side from the distal-end side of the groove, in substantially uniform groove width at the proximal end; a first electrode arranged at the proximal end side of the slit groove, and at least a part of the electrode is exposed to form a cutting part at the proximal end of the slit groove in order to be in contact with a living tissue to be cut; and a second electrode arranged at the other side opposite to the side where the first electrode of the tissue holding part is arranged, and arranged so as to hold at least a part of the tissue holding part on the body part.

DESCRIPTION OF THE PREFERRED EMBODIMENTS

First Embodiment

An Embodiment of the invention will be described in detail below with reference to the drawings.

The description will be made in the order of a blood vessel harvesting operation performing method using a living-tissue harvesting operation performing system, a configuration of the living-tissue harvesting operation performing system, and a harvester which is an instrument for cutting a living tissue according to a first embodiment of the present invention.

Figure 1:
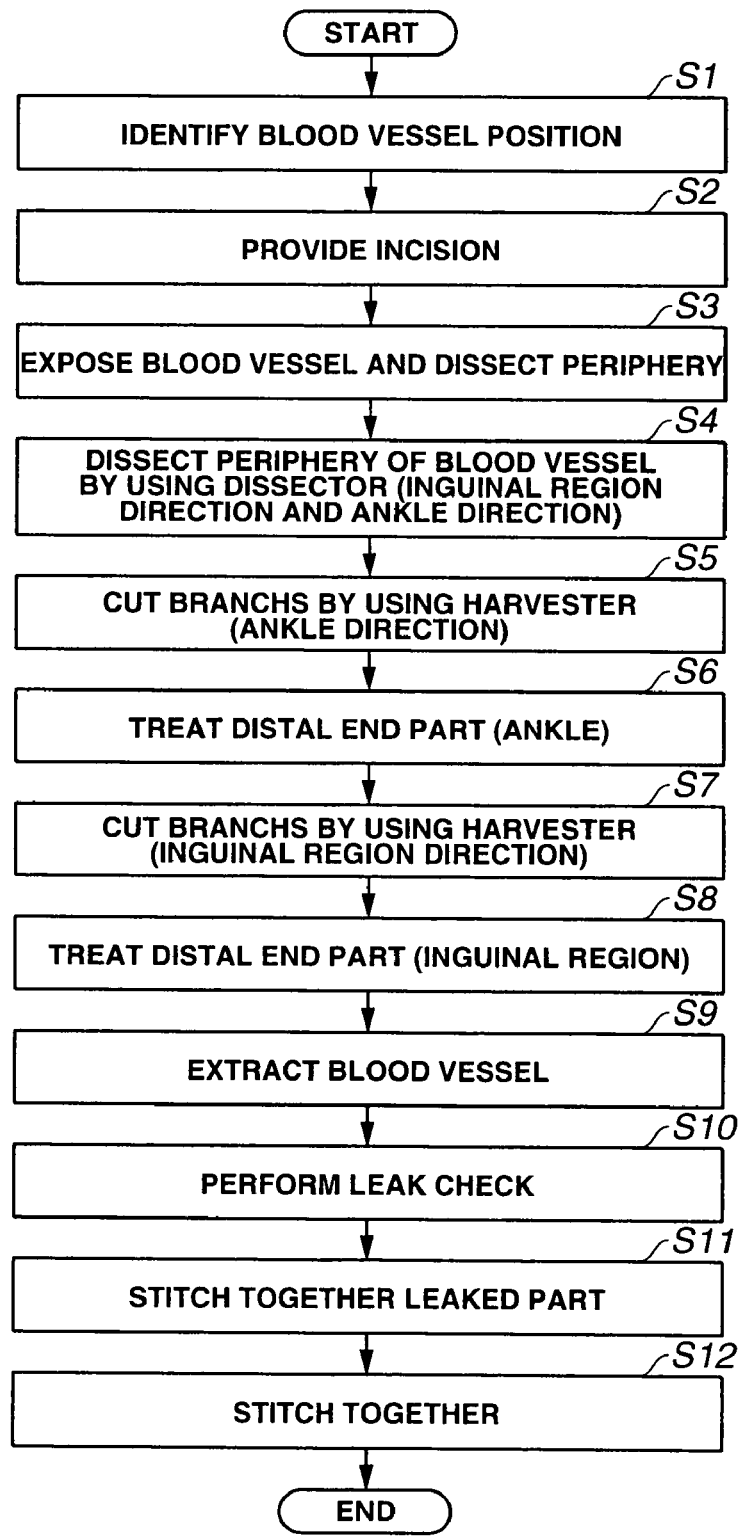
FIG. 1 is a flowchart for explaining an operation performing method of harvesting a subcutaneous vessel according to a first embodiment of the present invention.

First, an operation method for extracting a vein which is a target living tissue for harvesting by using a living-tissue harvesting apparatus will be described with reference to FIG. 1 through FIG. 6. FIG. 1 is a flowchart for explaining an operation performing method of harvesting a subcutaneous vessel. FIG. 2 through FIG. 6 are illustrations for explaining the operation performing method. The operation performing method of harvesting a blood vessel is described in accordance with FIG. 1, and with reference to FIG. 2 through FIG. 6.

In a Coronary Artery Bypass Grafting, a blood vessel in an inferior limb which is a harvesting target living tissue is used as a bypass blood vessel. Now, a description will be made regarding a case of harvesting an entire great saphenous vein extending from the thigh to the ankle (hereinafter, may be referred to as a blood vessel) which is a harvesting target blood vessel. As to instruments used for the harvesting, a dissector 31, trocar 21, and a harvester 41 will be described below in detail. In the dissector 31 and the harvester 41, an endoscope can be inserted, and an operator can sample the blood vessel while watching the endoscopic image. The endoscope is a rigid endoscope 51 shown in FIG. 7, which will be described in detail below, connected to a television monitor 102 via a television camera head connected to an eyepiece, and its endoscopic image is displayed on a screen of the television monitor 102. From a distal-end part of the rigid endoscope, illumination light is emitted and it is possible to illuminate a blood vessel 11 which is a subcutaneous tissue.

Figure 2:
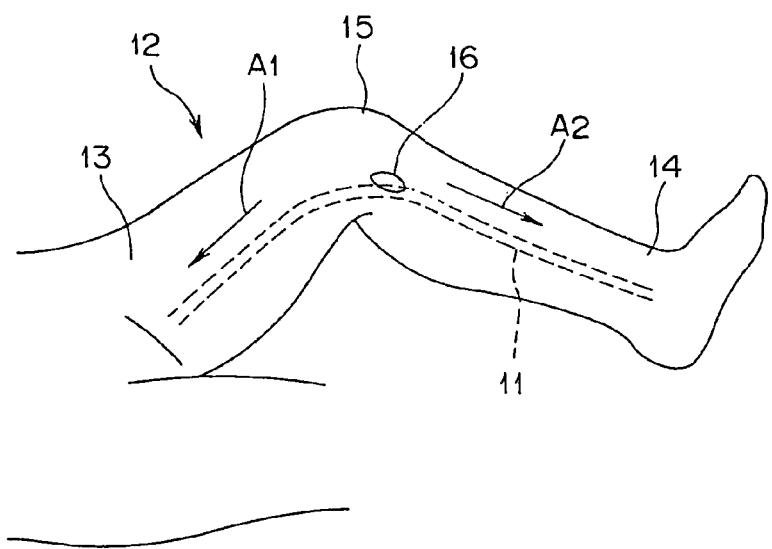
FIG. 2 is a view for explaining the operation performing method of harvesting a subcutaneous vessel according to the first embodiment of the present invention.

As shown in FIG. 2, the harvesting target blood vessel 11 exists between an inguinal region 13 of an inferior limb 12 and an ankle 14. The length of the blood vessel 11 to be sampled is, for example, 60 cm.

First, the operator identify the position of the blood vessel 11 (step (hereinafter, referred to as S) 1). The position of the blood vessel 11 is identified by a tactile impression of the operator or by using a device such as sonar. Then, in a direction substantially along the tube of the blood vessel 11, right above the identified blood vessel 11 and slightly below a knee 15, the operator provides an incision 16, for example, having the length of 2.5 cm, by a surgical knife, or the like (S2). Then, at the incision 16, the blood vessel 11 is exposed and peripheral tissues of the blood vessel 11 are dissected (S3).

Next, by using the dissector 31, the peripheral tissues of the entire length of the blood vessel 11 are dissected (S4). Specifically, the operator sets the trocar 21 to the incision 16, inserts the dissector 31 into a guiding tube part 22 of the trocar 21, while watching the endoscopic image, gradually inserts the dissector 31 from the incision 16 in the direction to the inguinal region 13 (indicated by the arrow A1), and bluntly dissects the blood vessel 11 form the peripheral tissues. The endoscopic image is necessary for the operator in order to dissect the peripheral tissues along the blood vessel 11.

When dissecting the peripheral tissues of the blood vessel 11, for example, when it is assumed that the position of the skin surface with respect to the blood vessel 11 is in an upward direction, the operator can completely dissect the peripheral tissues from the entire circumference of the blood vessel 11 by dissecting in the upward and downward directions of the blood vessel 11, and further rightward and leftward directions of the blood vessel. By dissecting the entire circumference of the blood vessel 11, it is possible to watch the branches of the blood vessel 11 more clearly in the endoscopic image.

When the dissecting of the blood vessel 11 from the peripheral tissues in the inguinal region 13 direction is completed, the dissector 31 is pulled out of the trocar 21. Then, the direction of the trocar of the incision 16 is changed, the dissector is gradually inserted from the incision 16 in the direction to the ankle 14 (indicated by the arrow A2), and the blood vessel 11 is dissected from the peripheral tissues while watching the endoscopic image.

Figure 3:
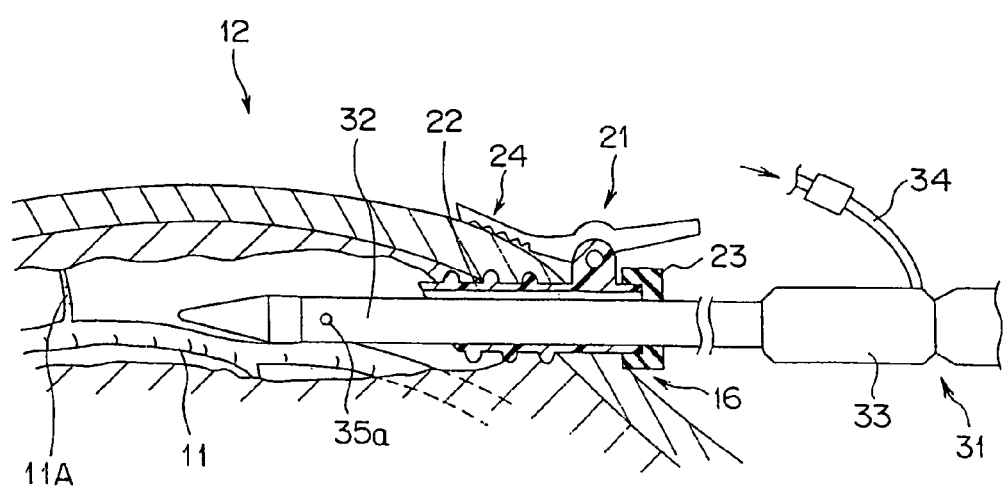
FIG. 3 is a sectional view illustrating a state in which a dissector is inserted into subcutaneous part of inferior limb from an incision in a direction to an inguinal region through a trocar according to the first embodiment of the present invention.

FIG. 3 is a sectional view illustrating a state in which the dissector is inserted into the subcutaneous part of the inferior limb 12 from the incision 16 in the direction to the inguinal region 13 via the trocar 21. The trocar 21 includes the tubular-shaped guiding tube part 22 used for inserting an insertion part 32 of the dissector 31, a seal part 23, and a fixing part 24 for fixing the trocar 21 to the skin. When setting the trocar 21 to the incision 16, the guiding tube part 22 is inserted from the incision 16 in the direction to the inguinal region, and fixed to the skin by a fixing part 24. The insertion part 32 of the dissector 31 is inserted into the subcutaneous part of the inferior limb 12 through the guiding tube part 22 of the trocar 21 fixed to the incision 16 by the fixing part 24. As will be described below, an endoscope insertion part is inserted in the insertion part 32. Since the insertion direction of the dissector 31 is along the direction of the blood vessel 11, the operator gradually inserts the dissector 31 while watching the endoscopic image in order to dissect the peripheral tissues of the blood vessel 11 from the blood vessel 11. That is, the insertion is not performed to reach directly an under part of the inguinal region 13 from the incision 16 along the blood vessel 11. By moving the dissector 31 forward and backward along the insertion direction, the dissectings of the blood vessel 11 is gradually performed up to the inguinal region 13 and up to the ankle 14.

Then, by an air supplying function provided to the dissector 31, carbon dioxide gas is supplied from an air supplying tube 34 connected to a grip part 33 of the dissector 31, and blown out from an opening part 35a provided at the distal-end part of the insertion part 32. Accordingly, while the blood vessel 11 is dissected from the peripheral tissues, the carbon dioxide gas exists between the dissected tissues and the blood vessel, and the operation visual field of the endoscope is widened and the visibility is improved. Thus, the operator becomes to be able to perform the dissecting operation easily.

Then, the dissector 31 is pulled out of the trocar 21, and while the trocar 21 is being left, then the harvester 41 (see FIG. 5) is inserted to perform a cutting operation of the branches of the blood vessel 11 from the incision 16 up to the ankle 14 (S5).

The cutting operation of the branches 11A, which are cutting target living tissues, is performed by inserting the harvester 41 from the incision 16 up to the under part of the ankle 14, and the branches 11A are cut one by one in the direction from the ankle 14 toward the incision 16.

The cutting of the branches 11A is performed by using a bipolar cutter 43 which is an electric knife provided at a distal-end part of the insertion part 42 of the harvester 41. The cut part of the branches 11A cut by the bipolar cutter 43 become substantially stanched state. By using the harvester 41, all of the branches 11A of the blood vessel 11 up to the ankle 14 are cut.

A configuration of the harvester 41 will be described below in detail. Here, a configuration will be described in brief. A vein keeper 45 is a blood vessel holding part provided at the distal-end part of the harvester 41 in order to hook the blood vessel 11. The vein keeper 45 of the harvester 41 has a mechanism that if hooking the blood vessel 11 on the vein keeper 45 is desired, a part of the vein keeper 45 is opened and the blood vessel 11 is hooked on the opened part, after the blood vessel 11 is hooked, the opened part is closed. Further, since the vein keeper 45 is movable in the axis direction of the harvester 41, and it is possible to move the vein keeper 45 in the direction separated from the distal-end part of the endoscope, the hooked blood vessel 11 can be easily seen in the endoscopic image.

Further, at the distal-end part of the bipolar cutter 43, a groove of 0.5 mm width is formed. When the branch 11A is cut, the branch 11A is pushed into the groove and cut in a compressed state. That is, the branch 11A is cut in the state that the branch 11A is crushed in the groove, thus, the branch 11A is ensured to be cut while the blood is being stanched. Moreover, at the distal-end part of the harvester 41, on the inside of a part surrounded by a wiper guard part, a wiper used for wiping extraneous matters adhered on a window part of the distal-end part of the rigid endoscope is provided. And, on a part of the cylindrical wiper guard, a sweeping opening for sweeping the extraneous matters wiped by the wiper is provided. As the extraneous matters, blood, fat, smoke due to the electric knife or the like can be considered.

The harvester 41 is also provided with the air supplying function, wherein carbon dioxide gas is supplied from a air supplying tube 44 connected to a grip part 400 of the harvester 41 to break out from an opening part (not shown) provided at the distal-end part of the insertion part 42. Accordingly, the cutting operation of the branches 11A becomes easier.

Since a plurality of the branches 11A exist in the blood vessel 11, while watching the endoscopic image at the distal end of the insertion part 42 of the harvester 41, the operator holds the blood vessel 11 by operating the vein keeper 45 at the distal end of the harvester 41, confirms the branches 11A one by one, and cuts the branches 11A by the bipolar cutter 43. A structure of the vein keeper 45 will be described below.

Then, a treatment of a termination of the blood vessel 11 is performed by providing a small incision, for example, the length of the incision is not greater than 1 cm, on the ankle 14, pulling the termination of the blood vessel 11 out of an incision 17, and tying the termination of the blood vessel 11 with a piece of string or indwelled with forceps (S6). In this case, the operator inserts the harvester 41 near the incision 17 again into the subcutaneous part of the ankle 14, and while watching the subcutaneous vessel 11 under the incision 17 and the forceps by using the endoscope, pinches the blood vessel 11 with the forceps, and pulls the blood vessel 11 out of the incision 17.

Figure 4:
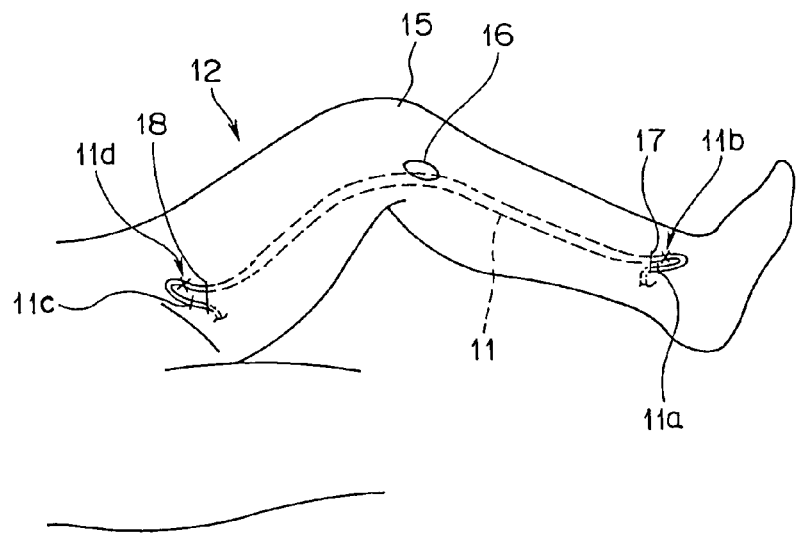
FIG. 4 is an illustration for explaining an operation performing method of harvesting a subcutaneous vessel according to the first embodiment of the present invention.

FIG. 4 is an illustration for explaining the treatment of the termination of blood vessel 11. The treatment of the termination of blood vessel 11 is performed by tying a part of the blood vessel 11 with a piece of string, and cutting the blood vessel 11 at a position 11b where is closer to the knee 15 than the knot 11a is. The incision at the incision 17 is closed by the operator with a tape or the like.

In the treatments of the termination of the blood vessel 11, the operator pulls the blood vessel 11 out of the incision 17 while watching the subcutaneous vessel under the incision 17 by the endoscope.

Then, the harvester 41 is pulled out of the trocar 21, the direction of the guiding tube part 22 of the trocar 21 of the incision 16 is changed to the direction to the inguinal region 13, the harvester 41 is inserted, and branches of the blood vessel 11 between the incision 16 and the inguinal region 13 are cut (S7). As well as S6, the operator cuts the branches 11A of the blood vessel 11 from the incision 16 to the inguinal region 13 while watching the endoscopic image.

Also, the cutting operation of the branches 11A is performed by the harvester 41 which is inserted from the incision 16 up to the under part of the inguinal region 13, and the branches 11A of the blood vessel 11 are cut one by one in the direction from the inguinal region 13 toward the incision 16.

Figure 5:
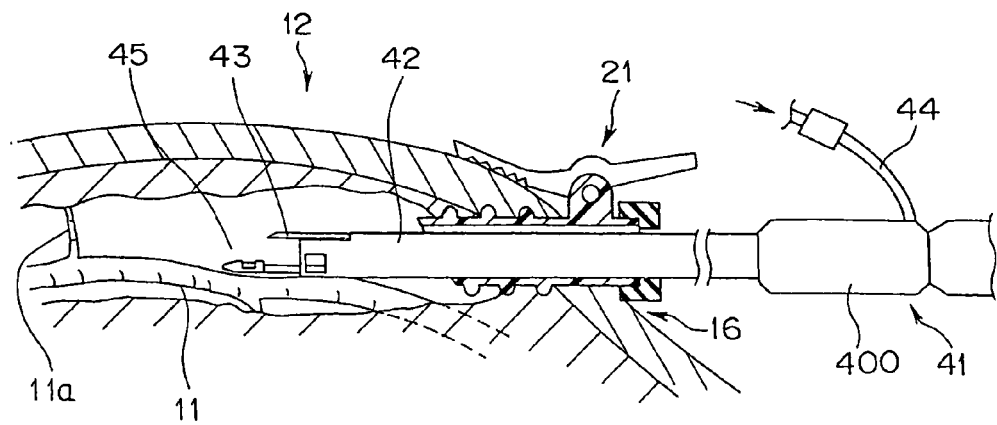
FIG. 5 is a sectional view illustrating a state in which a harvester is inserted into subcutaneous part of inferior limb from the incision through the trocar according to the first embodiment of the present invention.

FIG. 5 is a sectional view illustrating a state in which the harvester is inserted into the subcutaneous part of the inferior limb 12 from the incision 16 via the trocar 21. The insertion part 42 of the harvester 41 is inserted into the subcutaneous part of the inferior limb 12 through the guiding tube part 22 of trocar 21 fixed to the incision 16 by the fixing part 24. As will be described below, an endoscope insertion part is inserted in the insertion part 42. Since the insertion direction of the harvester 41 is along the direction of the blood vessel 11, the operator cuts the branches 11A while watching the endoscopic image.

When the cutting operation of the branches 11A is completed, as shown in FIG. 4, the treatment of a termination of the blood vessel is performed by providing a small incision, for example, the length of the incision is not greater than 1 cm, on the inguinal region 13, pulling the termination of the blood vessel 11 out of an incision 18, and tying the termination of the blood vessel 11 with a piece of string or indwelled with forceps (S8). Also in this case, the operator inserts the harvester 41 near the incision 16 again up to the subcutaneous part of the inguinal region 13 while watching the subcutaneous vessel 11 under the incision 18 and the forceps by the endoscope, pinches the blood vessel 11 with the forceps, and pulls the blood vessel 11 out of the incision 18. As well as the treatment at the incision 17 of the ankle 14, the treatment of the termination of blood vessel 11 is performed by tying a part of the blood vessel 11 with a piece of string, and cutting the blood vessel 11 at a position 11d where is closer to the knee 15 than the knot 11c is. The incision at the incision 18 is closed by the operator with a tape or the like.

Figure 6:
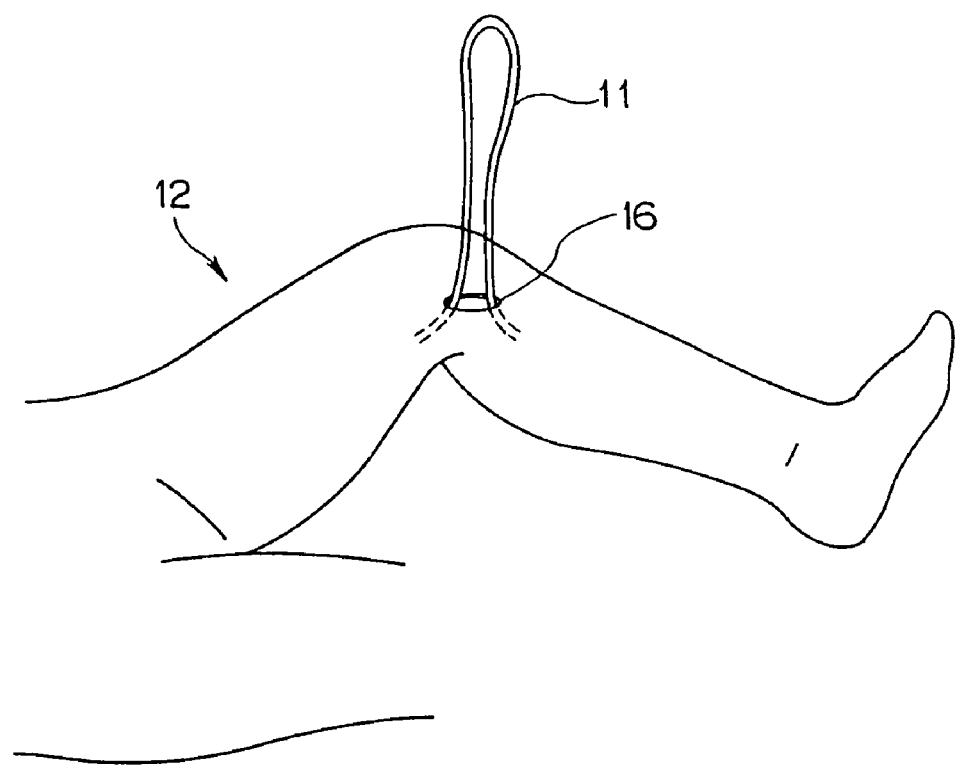
FIG. 6 is an illustration for explaining the operation performing method of harvesting a subcutaneous vessel according to the first embodiment of the present invention.

Then, as shown in FIG. 6, the operator extracts the blood vessel 11, for example, its length is 60 cm, from the incision 16 (S9). FIG. 6 is an illustration for explaining a state of extracting the blood vessel 11 from the incision 16. When the extraction of the blood vessel 11 is completed, the operator performs a leak check of the blood vessel 11 because if there is an opening on the extracted blood vessel 11, it is not possible to use the blood vessel 11 as a blood vessel to be used for a bypass (S10).

While performing the leak check, the operator stitches all of the branches 11A of the blood vessel 11 in order to prevent the cut terminals of the branches 11A from blood leaking. In the state in which all of the branches 11A are tied with a piece of string, in consideration of the direction of valves in the blood vessel 11, a syringe is attached to one end of the blood vessel 11, physiological saline is passed into the blood vessel 11, and by checking whether there is an opening from where the physiological saline is leaking or not, the operator performs the leak check of the blood vessel 11.

If there is an opening from where the physiological saline is leaking, the opening is stitched together (S11). Finally, the incision 16 is stitched together (S12).

As described above, compared with a known operation in which tissues of a certain part of the inferior limb 12 are incised in a state that the entire blood vessel 11 from the inguinal region 13 of the inferior limb 12 through the ankle 14 can be seen, the above-described method for extracting the blood vessel by using the endoscope is minimally invasive to a patient because, for example, the incisions are only three. It can be possible, for example, to reduce the period of time required until the patient becomes to be able to walk after the operation.

Next, a living-tissue harvesting operation performing system will be described with reference to FIG. 7.

Figure 7:
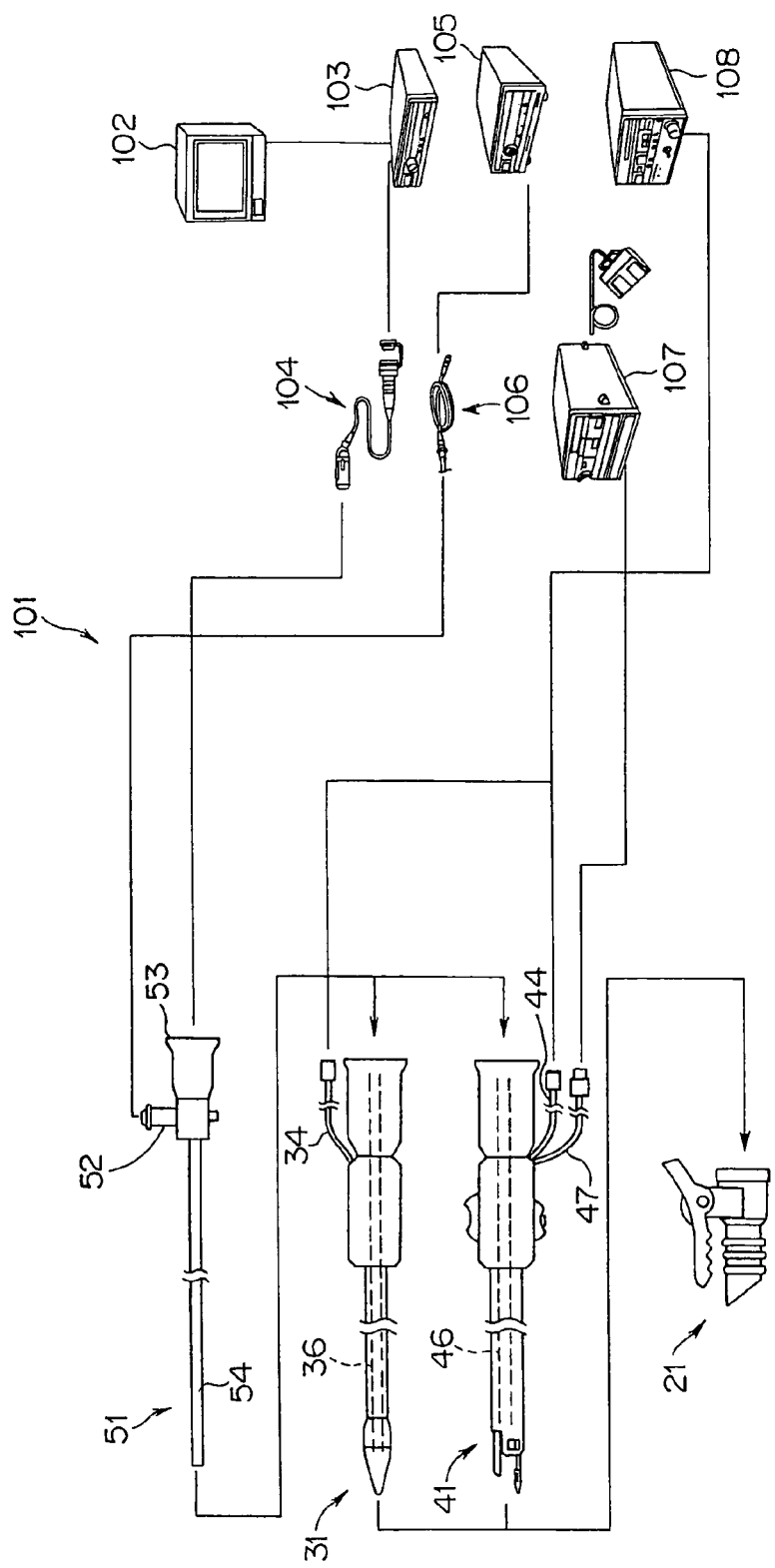
FIG. 7 is a constitutional view illustrating a configuration of a living-tissue harvesting operation performing system composed of devices and instruments used for the operation of harvesting a subcutaneous vessel according to the first embodiment of the present invention.

FIG. 7 is a constitutional view illustrating a configuration of the living-tissue harvesting operation performing system composed of devices and instruments used for the above-described operation, or the like. A living-tissue harvesting operation performing system (hereinafter referred to as operation performing system) 101 includes the above-described trocar 21, dissector 31, which is a device for dissecting a living tissue, the harvester 41, which is an instrument for cutting a living tissue, and the rigid endoscope 51, which is an endoscope. The operation performing system 101 further includes a television monitor 102, which is a display device, a camera control unit (hereinafter referred to as CCU) 103, a television camera device 104, a light source device 105, a light guide cable 106, an electric knife device 107, and an air supplying device 108.

To a light guide connecter part 52 of the rigid endoscope 51, one end of the light guide cable 106 is connected. The other end of the light guide cable 106 is connected to the light source device 105. To the rigid endoscope 51, light from the light source device 105 is supplied via the light guide cable 106 in which a light guide of optical fiber is inserted, and an subject is illuminated from the distal-end part of the rigid endoscope 51. A camera head part of the television camera device 104 is connected to an eyepiece part 53 of a proximal end side of the rigid endoscope 51. The television camera device 104 is connected to the CCU 103, and an image of the subject obtained by the rigid endoscope 51 is displayed on a screen of the television monitor 102.

A distal-end insertion part 54 of the rigid endoscope 51 can be inserted into a rigid endoscope insertion channel 36 from a proximal end side of the dissector 31. Similarly, the distal-end insertion part 54 of the rigid endoscope 51 can be inserted into a rigid endoscope insertion channel 46 which is inserted in an insertion part 42 of the harvester 41, which will be described below, from a proximal end side of the harvester 41.

An air supplying tube 34 of the dissector 31 is connected to the air supplying device 108, receives carbon dioxide gas supplied from the air supplying device 108, and discharges the carbon dioxide gas from an opening 35A which is an air supplying outlet.

An air supplying tube 44 of the harvester 41 is also connected to the air supplying device 108, receives carbon dioxide gas supplied from the air supplying device 108, and discharges the carbon dioxide gas from an opening (not shown in FIG. 7) which is an air supplying outlet.

The harvester 41 has an electrical cable 47 for the bipolar cutter 43. By a connecter provided at a proximal end side of the electrical cable 47, the harvester 41 is connected to the electric knife device 107.

By using the operation performing system 101 having the configuration, the operator can perform the above-described operation.

Now, the harvester which is an instrument for cutting a living tissue according to the first embodiment of the present invention will be described with reference to FIG. 8 through FIG. 18.

Figure 8:
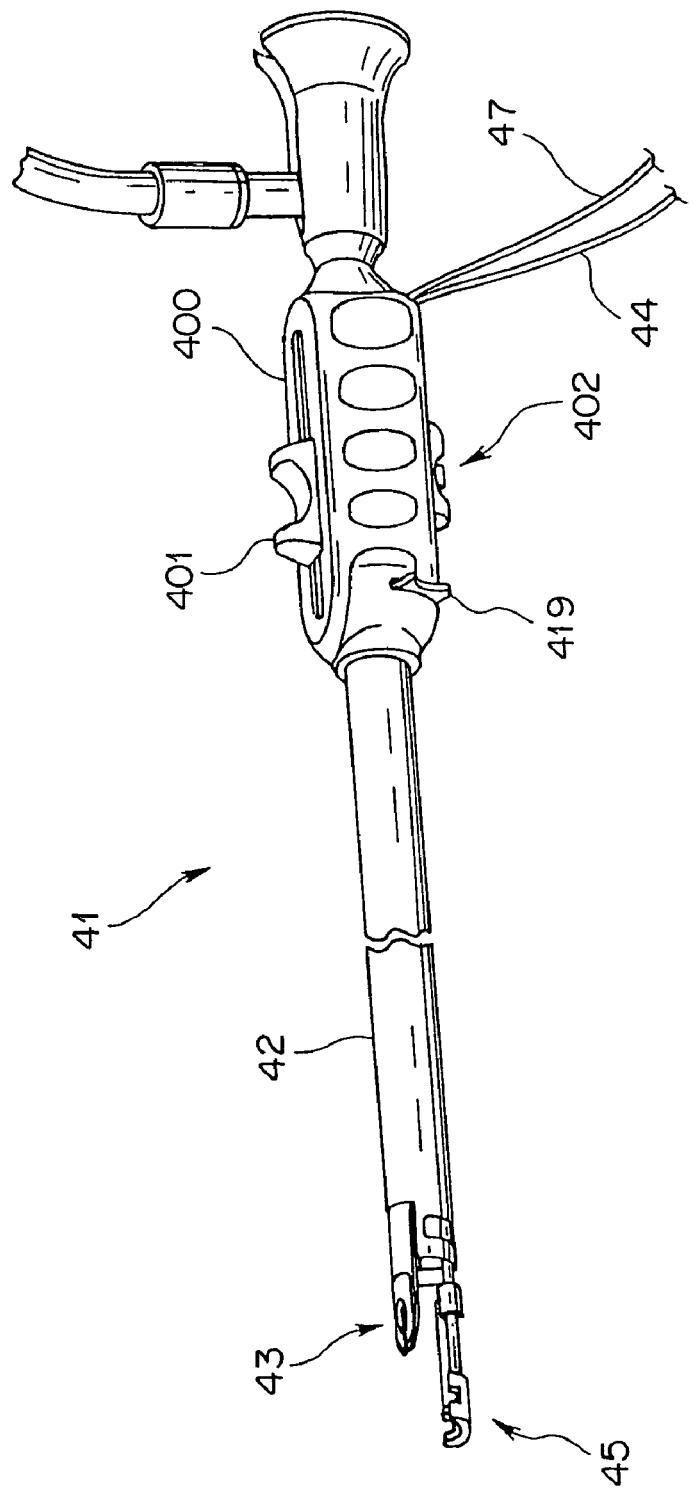
FIG. 8 is a side view of the harvester according to the first embodiment of the present invention.

FIG. 8 is a side view of the harvester 41. On a distal-end part of the insertion part 42, which is made of a metal, of the harvester 41, the bipolar cutter 43 is provided at its upper part and the vein keeper 45, which is a holder, is provided at the inside of its lower part. Upon a bipolar cutter lever 401 and a vein keeper lever 402 which are operating members provided on a grip part 400 consecutively provided to the proximal end of the insertion part 42, are moved forward and backward in the direction along the longitudinal direction, in interlocking with the movements, the bipolar cutter 43 and the vein keeper 45 can be moved forward and backward toward the front of the insertion part 42.

Figure 9:
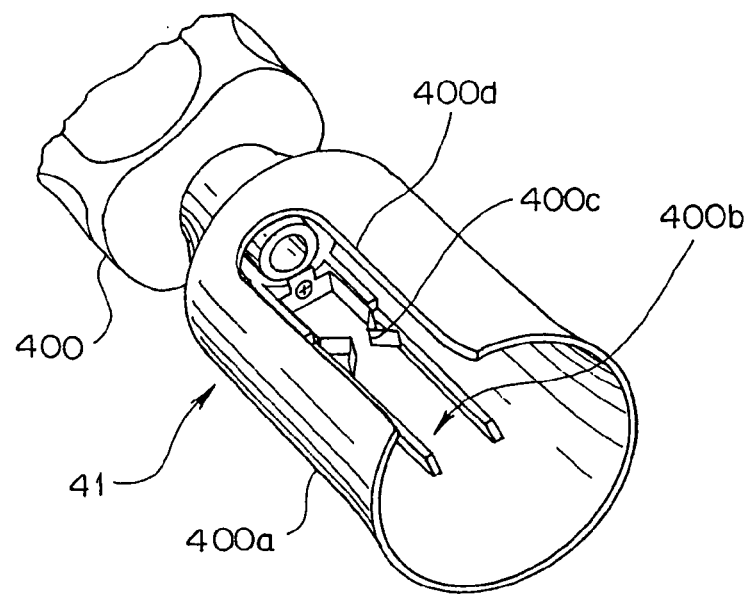
FIG. 9 is a partial perspective view for explaining a structure of the proximal end side of the harvester according to the first embodiment of the present invention.

FIG. 9 is a partial perspective view for explaining a configuration of the proximal end side of the harvester 41. In the configuration of the proximal end side of the harvester 41, as shown in FIG. 9, a guiding groove 400b is provided on the inner circumference surface of a proximal end part 400a of the harvester 41 in the direction along the axis of the harvester 41 in order to facilitate and ensure the fixation of the rigid endoscope 51 to the proximal end part of the harvester 41. Further, to the guiding groove 400b, a fixing member 400c is screwed. The fixing member 400c is formed by bending a plate-shaped member made of a metal into U-shape, further bending the both ends of the U-shape toward the inside of the U-shape so as to have a convex-shaped part. On the other hand, at a distal-end side of an eyepiece 53 of the rigid endoscope 51, a convex part (not shown) is provided.

Further, a notched part 400d is provided on the proximal end part 400a and a light guide connector part 52 can move along the notched part 400d.

When the rigid endoscope 51 is inserted from the proximal end part of the harvester 41, the rigid endoscope 51 is inserted such that the convex part of the rigid endoscope 51 is entered along the guiding groove 400b provided on the inner circumference surface of a proximal end part 400a, and the light guide connector part 52 is entered along the notched part 400d. When the rigid endoscope 51 is being inserted from the proximal end part of the harvester 41, the convex part of the rigid endoscope 51 is moved along the inside of the guiding groove 400b, and moved ahead of the convex-shaped part of the fixing member 400c made of the metal against the elastic force of the fixing member 400c. Then, the light guiding connector part 52 is also moved along the notched part 400d provided on the proximal end part 400a.

Accordingly, when inserting the rigid endoscope 51 from the proximal end part of the harvester 41, the physical relationship between the harvester 41 and the rigid endoscope 51 is set such that the light guide connector part 52 enters in the notched part 400d and the convex part of the rigid endoscope 51 enters in the guiding groove 400b, and then, the rigid endoscope 51 is inserted into the harvester 41. When the rigid endoscope 51 is being inserted into the harvester 41, the convex part of the rigid endoscope 51 is engaged and fixed in a sandwiched manner by the fixing member 400c in the middle of the insertion, and the convex part of the rigid endoscope 51 becomes not readily fallen off with the elastic force of the fixing member 400c.

Further, when the convex part of the rigid endoscope 51 is engaged and fixed, between the rigid endoscope 51 and the harvester 41, sound implying that the rigid endoscope 51 is engaged arises, and the user can confirm that the rigid endoscope 51 is set by the sound.

Figure 10:
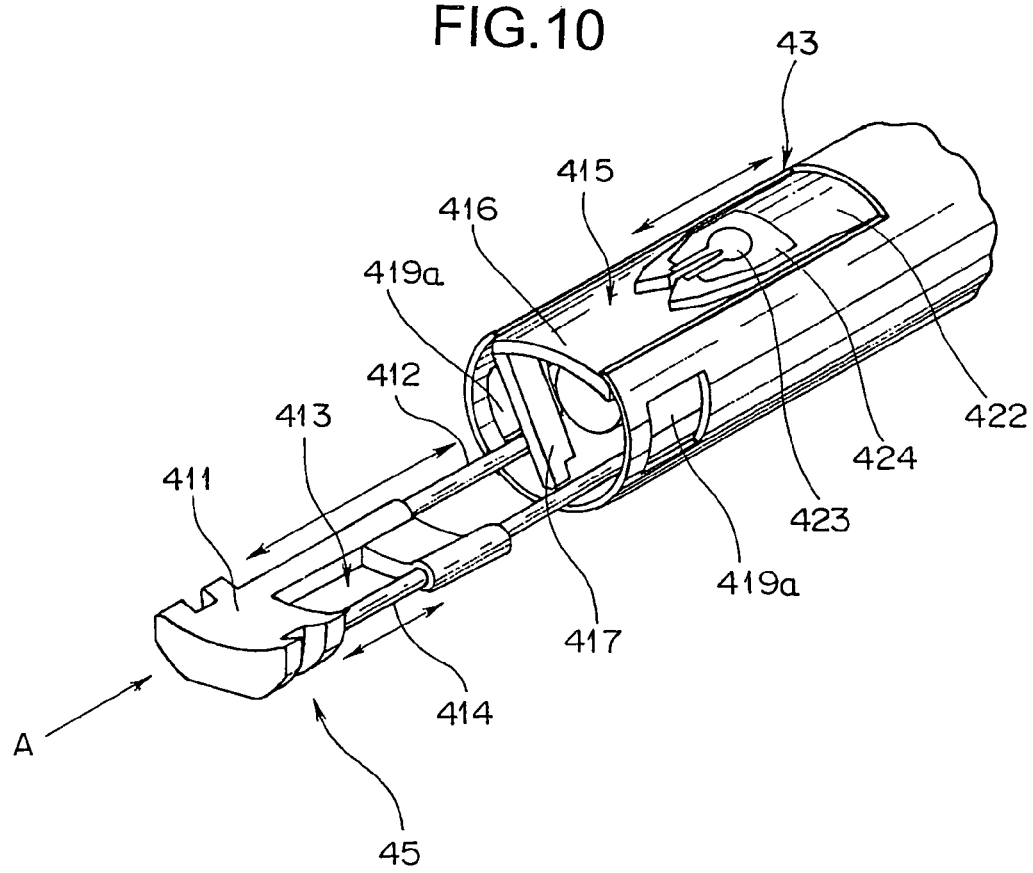
FIG. 10 is a partial perspective view illustrating a structure of a distal end of the harvester according to the first embodiment of the present invention.
Figure 11:
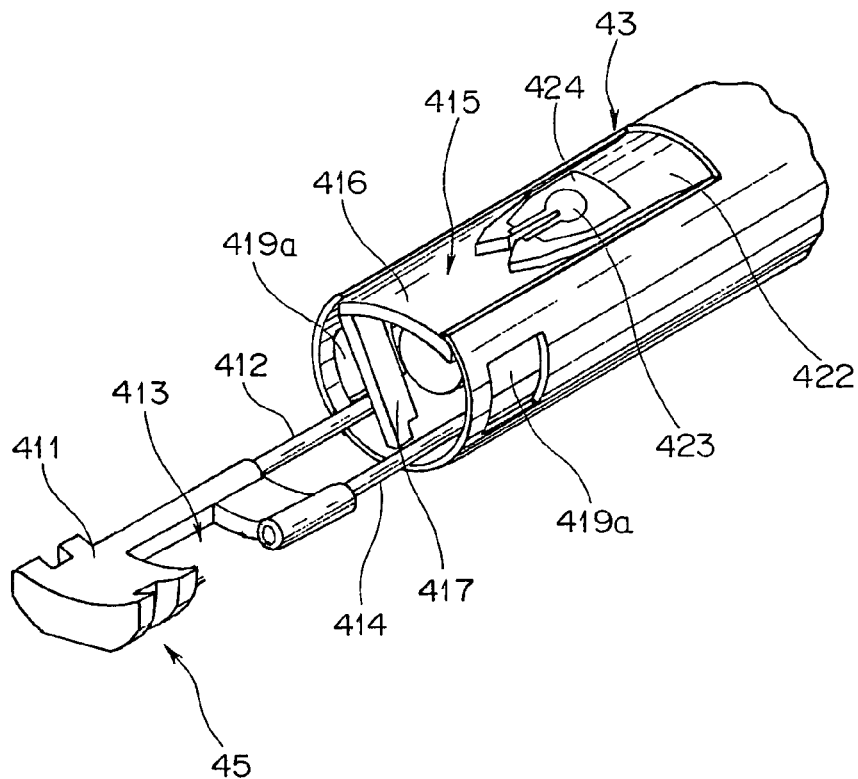
FIG. 11 is an illustration for explaining operation of a lock bar shown in FIG. 10 according to the first embodiment of the present invention.
Figure 12:
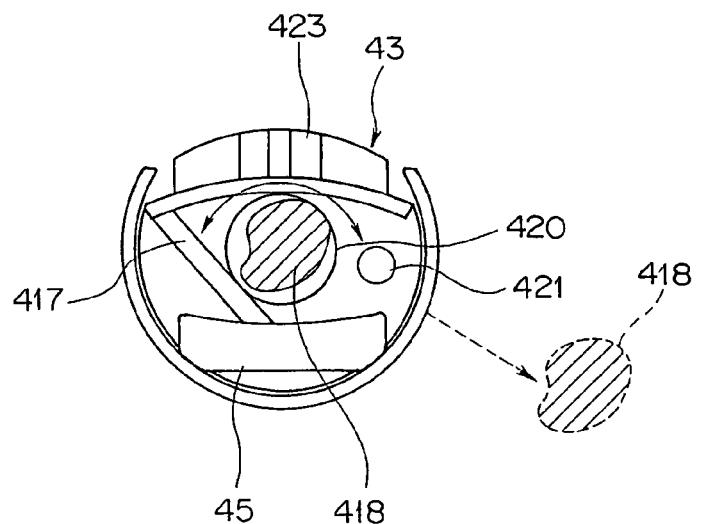
FIG. 12 is an illustration viewed from the direction of the arrow A in FIG. 10 according to the first embodiment of the present invention.

FIG. 10 is a partial perspective view illustrating a structure of the distal end of the harvester 41, FIG. 11 is an illustration for explaining operation of a lock bar shown in FIG. 10, and FIG. 12 is an illustration viewed from the direction of the arrow A in FIG. 10.

As shown in FIG. 10, the vein keeper 45 of the harvester 41 is composed of a vein keeper rod 412 which holds a substantially U-shaped blood vessel holding base 411 to be movable forward and backward in the longitudinal axis direction, and a lock bar 414 which is movable forward and backward in the longitudinal axis direction against the blood vessel holding base 411 which forms a closed space 413 housing the blood vessel on the substantially U-shaped blood vessel holding base 411 which is parallel to the vein keeper rod 412. The lock bar 414, in a state shown in FIG. 10, forms the space 413 in a state locked to the blood vessel holding base 411 as well as the vein keeper rod 412. However, by releasing the locked state of the lock bar 414, as shown in FIG. 11, it is possible to release the closed space 413 and the lock bar 414 can move forward and backward capably of housing the blood vessel 11 in the closed space 413.

On the distal-end side surface of the insertion part 42 on which the bipolar cutter 43 is provided, a notch 415 is provided, and a cutter axis (described below) which moves the bipolar cutter 43 forward and backward is inserted into the insertion part 42 through the notch 415. On the inner wall surface of the notch 415, a guard part 416 having an arc-shaped cross section is provided and on the inner surface of the distal end of the insertion part 42, a wiper 417 for wiping an extraneous matter adhered to a window part of the distal-end part of the rigid endoscope 51 is provided. The wiper guard part is formed such that one end of the wiper 417 serves as an axis and the other end sweeps the inside of the guard part 416. At one part of the cylindrical-shaped wiper guard part, a sweeping opening 419a for sweeping the extraneous matter 418 (see FIG. 12) wiped by the wiper 417 is provided. As the extraneous matter, blood, fat, smoke due to the electric knife or the like can be considered.

Figure 16:
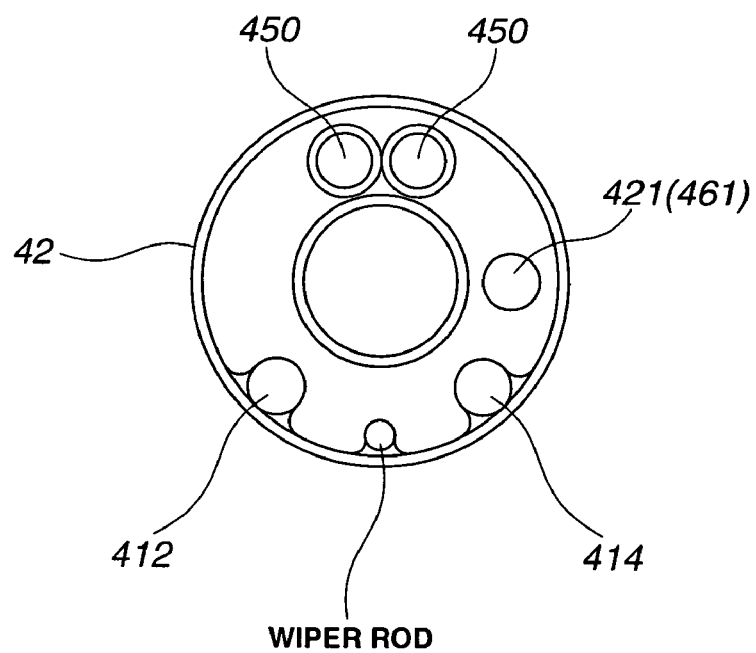
FIG. 16 is a sectional view taken along the XVI-XVI line shown in FIG. 15 according to the first embodiment of the present invention.

The wiper 417 sweeps by operating a wiper lever 419 (see FIG. 8) via a wiper rod (not shown, see FIG. 16).

As shown in FIG. 12 which is an illustration viewed from the direction of the arrow A in FIG. 10. At a position inside from the distal-end surface of the insertion part 42 by a predetermined distance, an opening of a rigid endoscope insertion channel 420 in which the rigid endoscope 51 is inserted and an opening of an air supplying channel 421 are adjacently provided.

Figure 13:
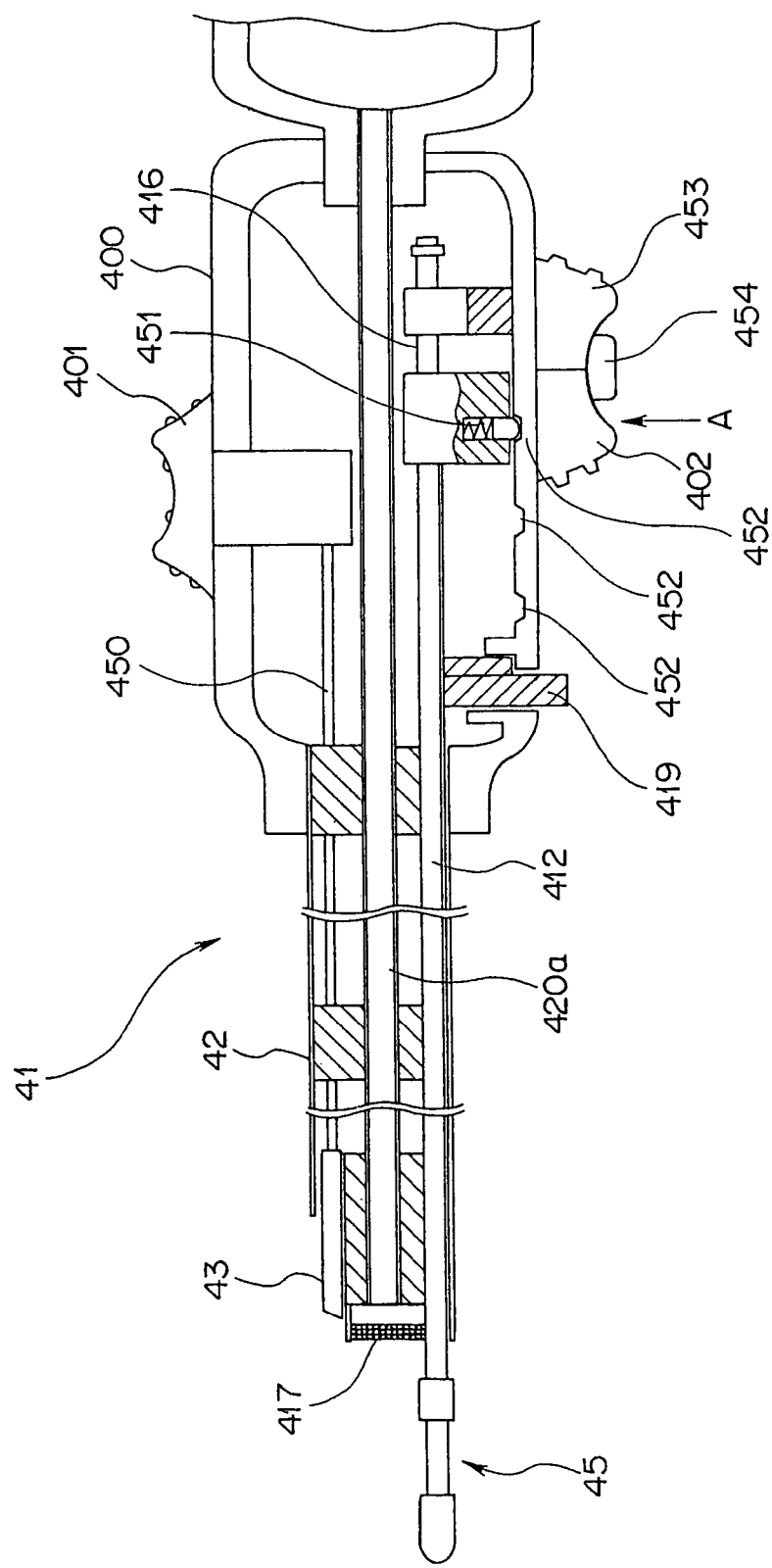
FIG. 13 is a sectional view in the direction of the long axis illustrating an operating configuration of the harvester according to the first embodiment of the present invention.
Figure 14:
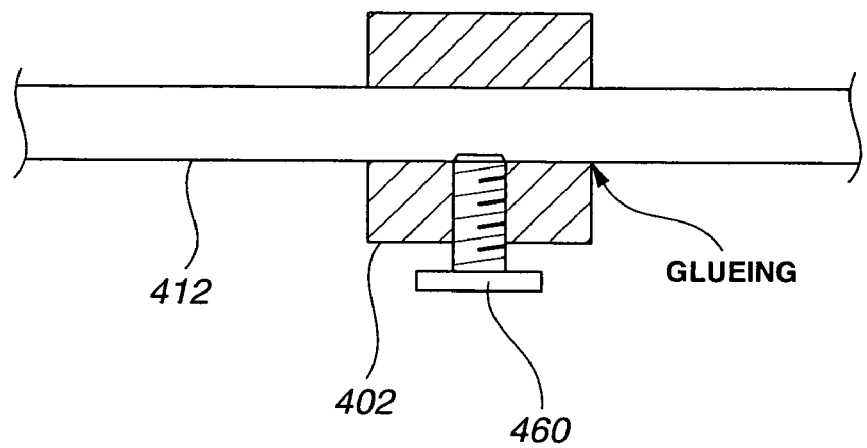
FIG. 14 is a conceptual view on attaching of a vein keeper lever, viewed from the direction of the arrow A shown in FIG. 13 according to the first embodiment of the present invention.

FIG. 13 is a sectional view in the direction of the long axis illustrating an operating configuration of the harvester 41, and FIG. 14 is a conceptual view on attaching the vein keeper lever 402, viewed from the direction of the arrow A shown in FIG. 13.

As shown in FIG. 13, along the axis direction of the harvester 41, a metal tube member 420a which forms the rigid endoscope insertion channel 420 is inserted in the inside of the harvester 41 from the proximal end side of the grip part 400 through the distal-end part of the insertion part 42. The bipolar cutter 43 is connected to the bipolar cutter lever 401 provided on the grip part 400 via a bipolar rod 450 which is inserted through the insertion part 42. When the bipolar cutter lever 401 is moved forward and backward along the longitudinal axis, the force of the movement is transmitted to the bipolar cutter 43 via the bipolar rod 450, and it is possible to move forward and backward the bipolar cutter 43 toward the front of the insertion part 42.

Similarly, the vein keeper 45 is connected to the vein keeper lever 402 provided on the grip part 400 via a vein keeper rod 412 which is inserted through the insertion part 42. When the vein keeper lever 402 is moved forward and backward along the longitudinal axis, the force of the movement is transmitted to the vein keeper 45 through the vein keeper rod 412, and it is possible to move forward and backward the vein keeper 45 toward the front of the insertion part 42.

The vein keeper lever 402 and the vein keeper lever 412 are integrally movable in the inner surface of the grip part 400 by a click assembly 451 which pin-presses the inner surface of the grip part 400, wherein if the click assembly 451 positions, for example, one of three click grooves 452 provided at the inner surface of the grip part 400, the vein keeper lever 402 and the vein keeper rod 412 can be stably held at the position, and by adding force to the longitudinal axis, the click assembly 451 can be readily thrown out from the click groove 452.

The vein keeper 402 is freely detachably connected to the lock lever 453, and by depressing a lock button 454, the vein keeper 402 can be separated from the lock lever 453. The lock lever 453 is connected to the lock lever 414, and by moving forward and backward the lock lever 453 in a state being separated from the vein keeper lever 402, the lock lever 453 can be moved forward and backward capably of housing the blood vessel 11 within the closed space 413 (see FIG. 10 and FIG. 11).

As shown in FIG. 14, the vein keeper lever 402 is strongly fixed to the vein keeper rod 412 by screw 460 and gluing.

Figure 15:
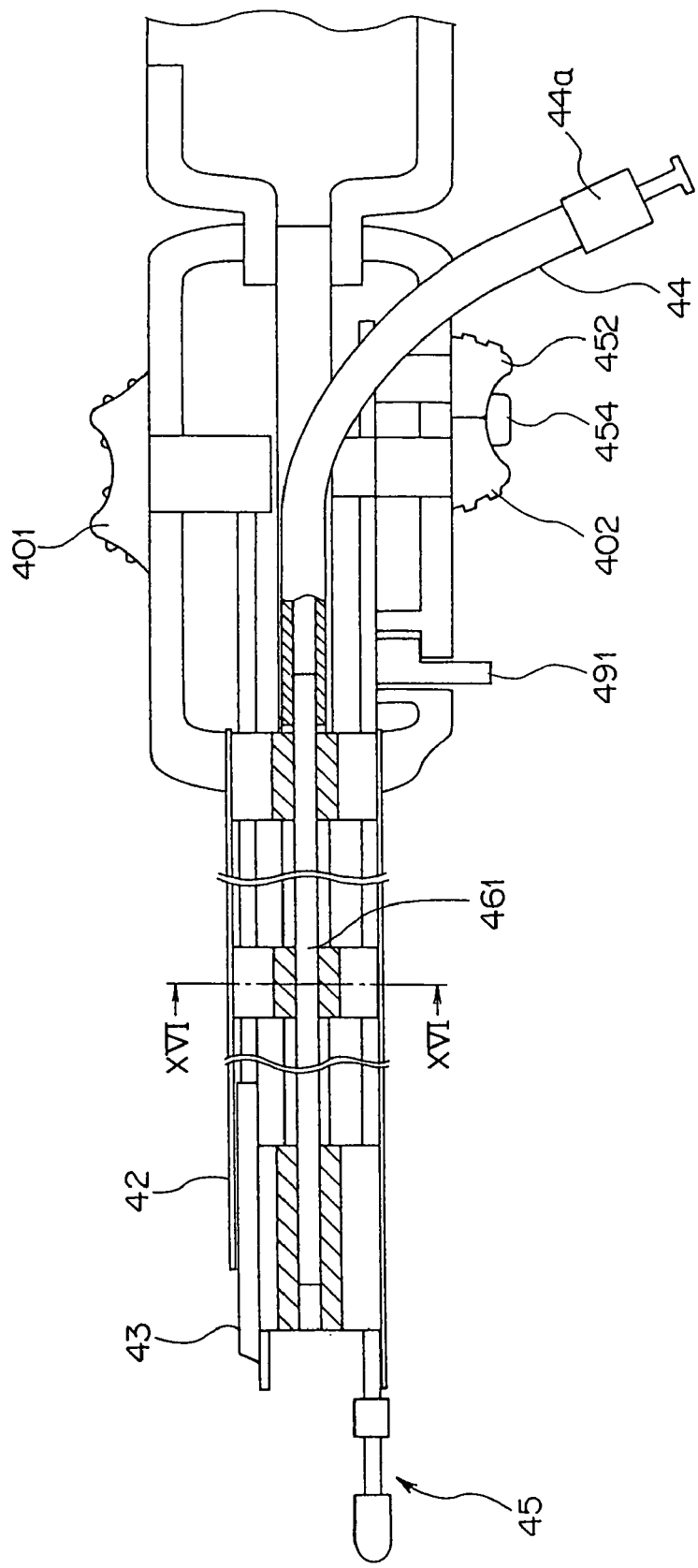
FIG. 15 is a sectional view in the direction of the long axis, illustrating an air supplying configuration of the harvester according to the first embodiment of the present invention.
Figure 17:
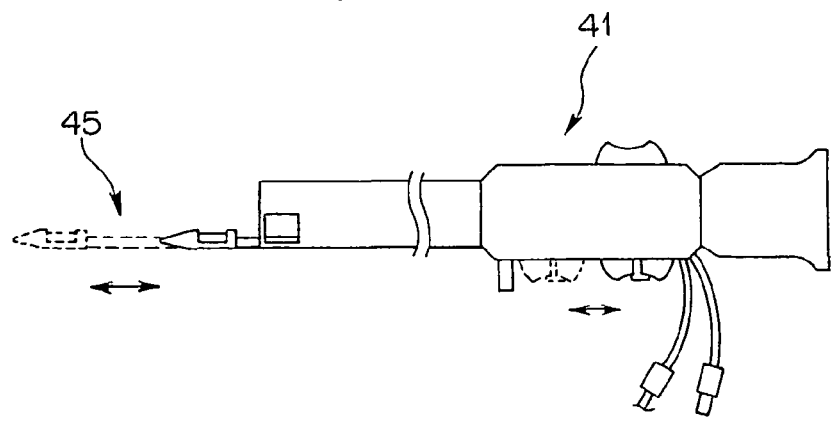
FIG. 17 is an illustration for explaining forward and backward movement of a vein keeper, the movement being generated by operating the vein keeper lever, according to the first embodiment of the present invention.
Figure 18:
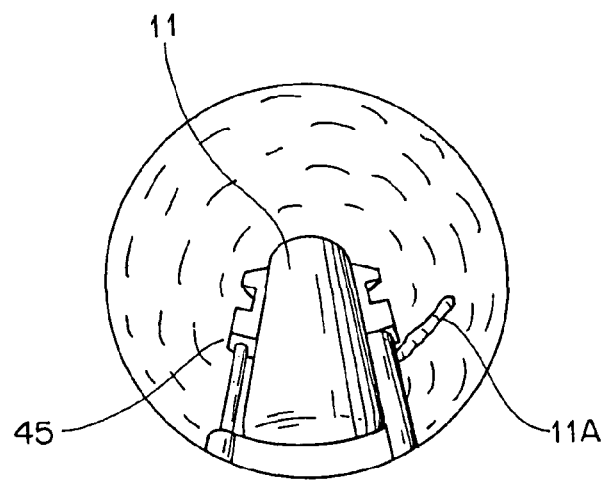
FIG. 18 is an endoscopic image upon cutting a branch according to the first embodiment of the present invention.

FIG. 15 is a sectional view in the direction of the long axis illustrating an air supplying configuration of the harvester 41, and FIG. 16 is a sectional view taken along the XVI-XVI line shown in FIG. 15.

As shown in FIG. 15, along the axis direction of the harvester 41, an air supplying pipe 461 made of a metal which forms an air supply channel 421 is inserted in the harvester 41 from the proximal end side of the grip part 400 through the distal-end part of the insertion part 42. At one end of the air supplying pipe 461 of the grip part 400, an air supplying tube 44 is fitted into in the grip part 400, an air supplying connector 44a is provided at a proximal end of the air supplying tube 44, and the air supplying connector 44a is connected to a connector of a tube connected to the air supplying device 108.

Figure 19:
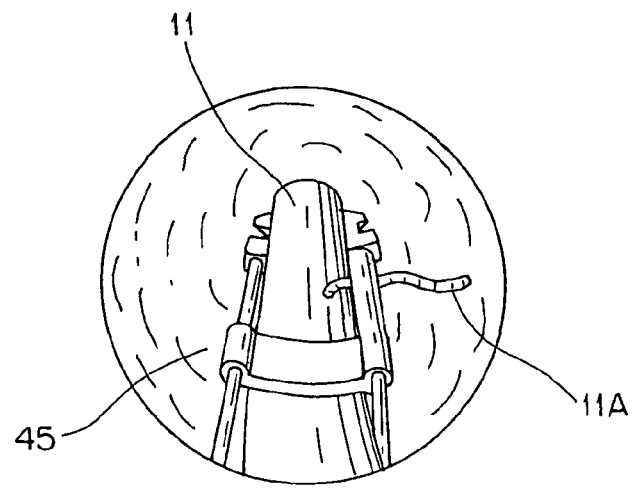
FIG. 19 is an endoscopic image upon cutting a branch according to the first embodiment of the present invention.

As described above, in the first embodiment, as shown in FIG. 17, by moving the vein keeper lever 402 forward and backward, it is possible to move the vein keeper 45 forward and backward at the distal end. Accordingly, for example, as shown in an endoscopic image in FIG. 18, if a state of the branch 11A is hard to see when cutting the branch 11A, by moving the vein keeper lever 402 forward in the longitudinal axis direction as shown in FIG. 19, the distal end of the vein keeper 45 moves forward, and it is possible to see an endoscopic image suitable for confirming the state of the branch 11A.

Now, the bipolar cutter 43 which is inserted in the harvester 41 will be described with reference to FIG. 20 through FIG. 24.

Figure 20:
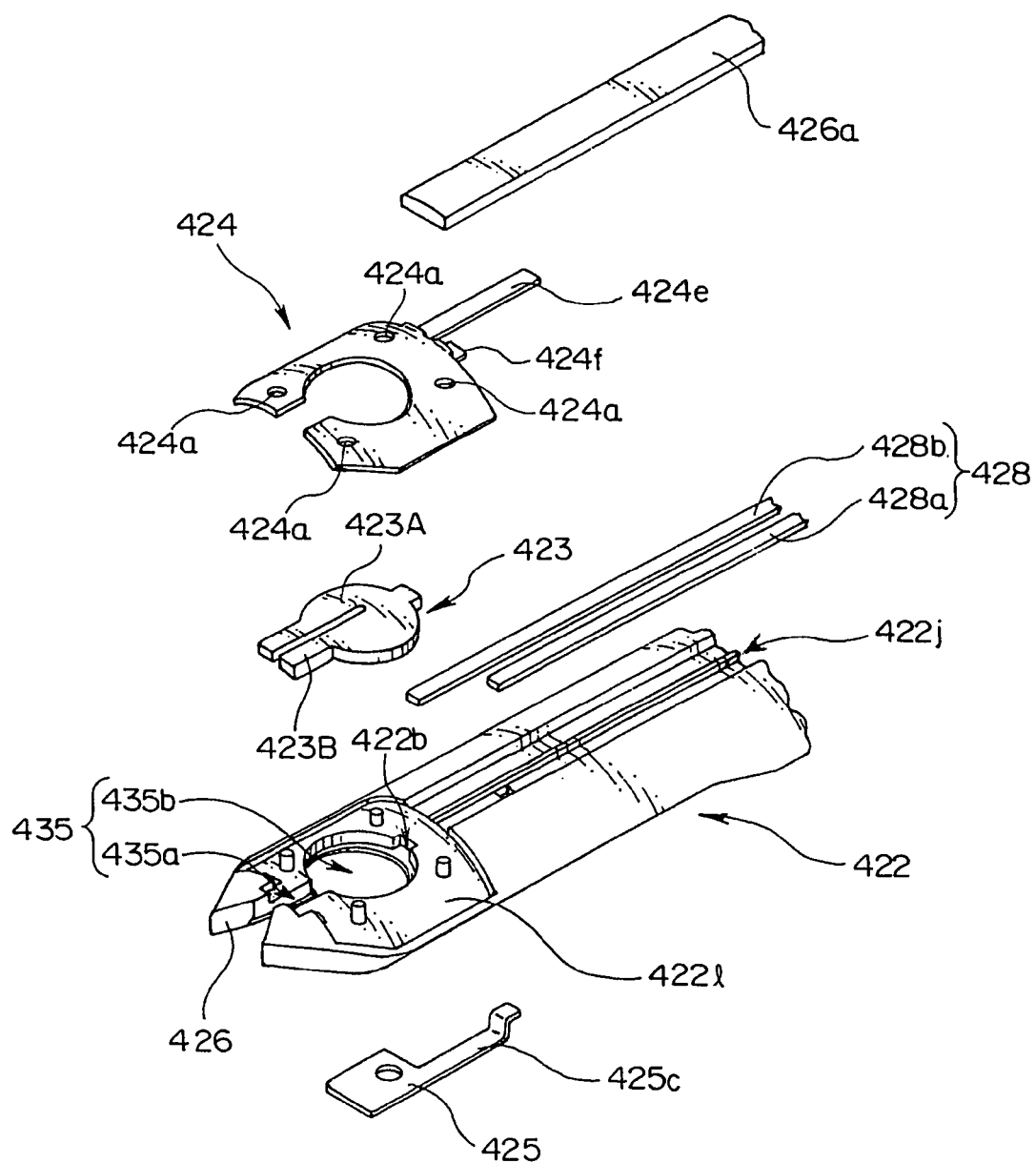
FIG. 20 is an exploded perspective view of a distal-end part of a bipolar cutter according to the first embodiment of the present invention.
Figure 21:
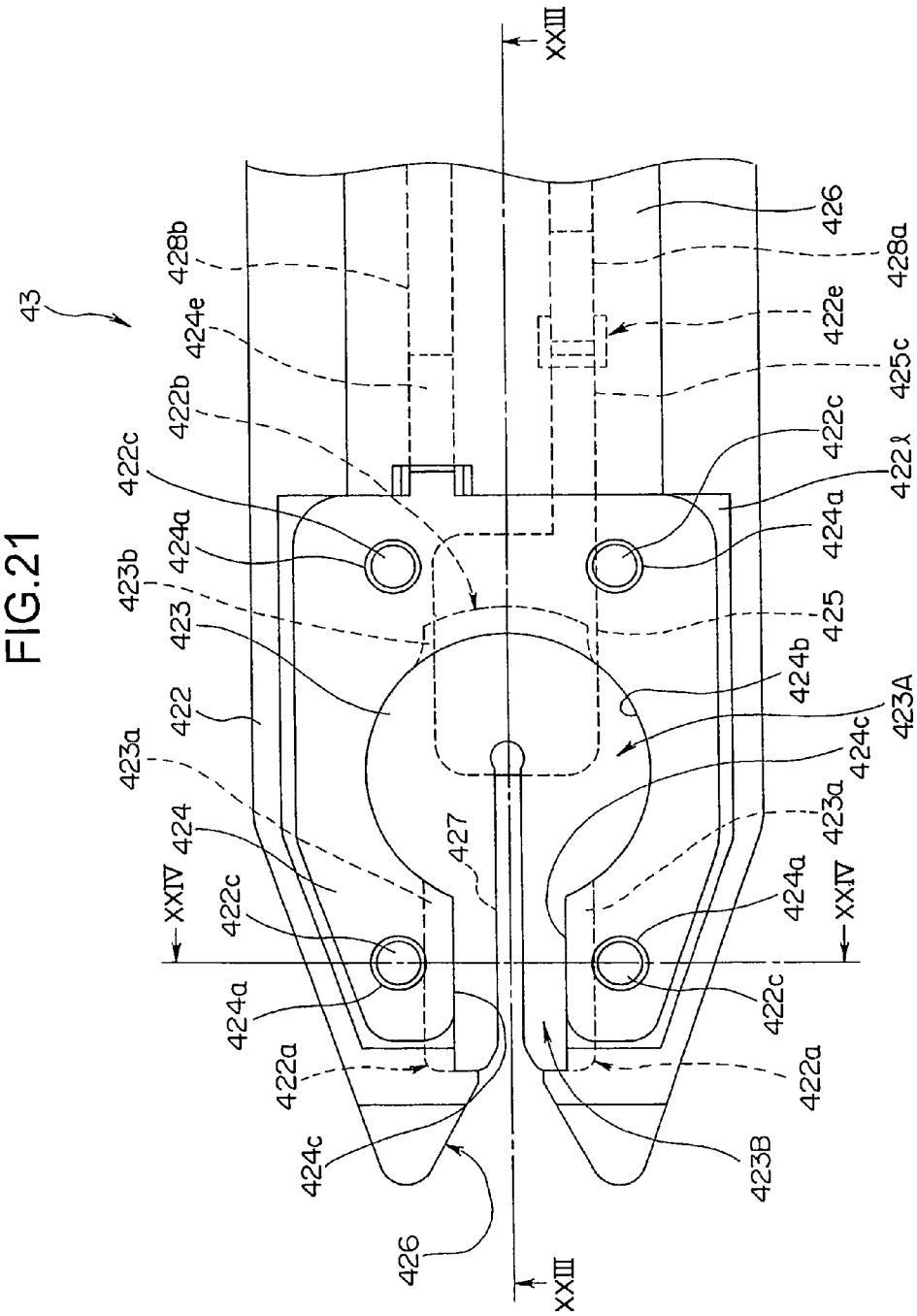
FIG. 21 is an illustration of the top surface of the bipolar cutter according to the first embodiment of the present invention.
Figure 22:
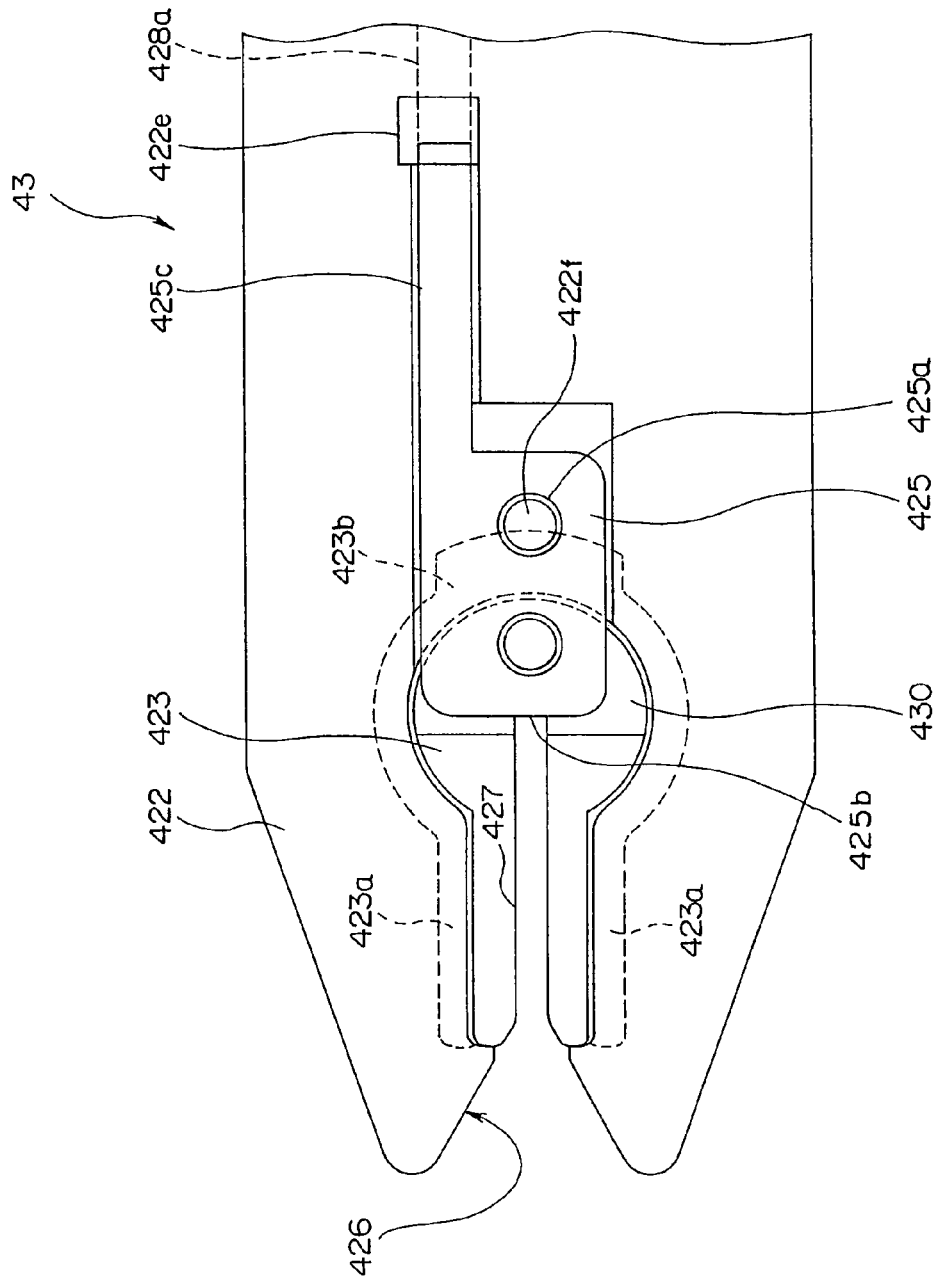
FIG. 22 is an illustration of the undersurface of the bipolar cutter according to the first embodiment of the present invention.
Figure 23:
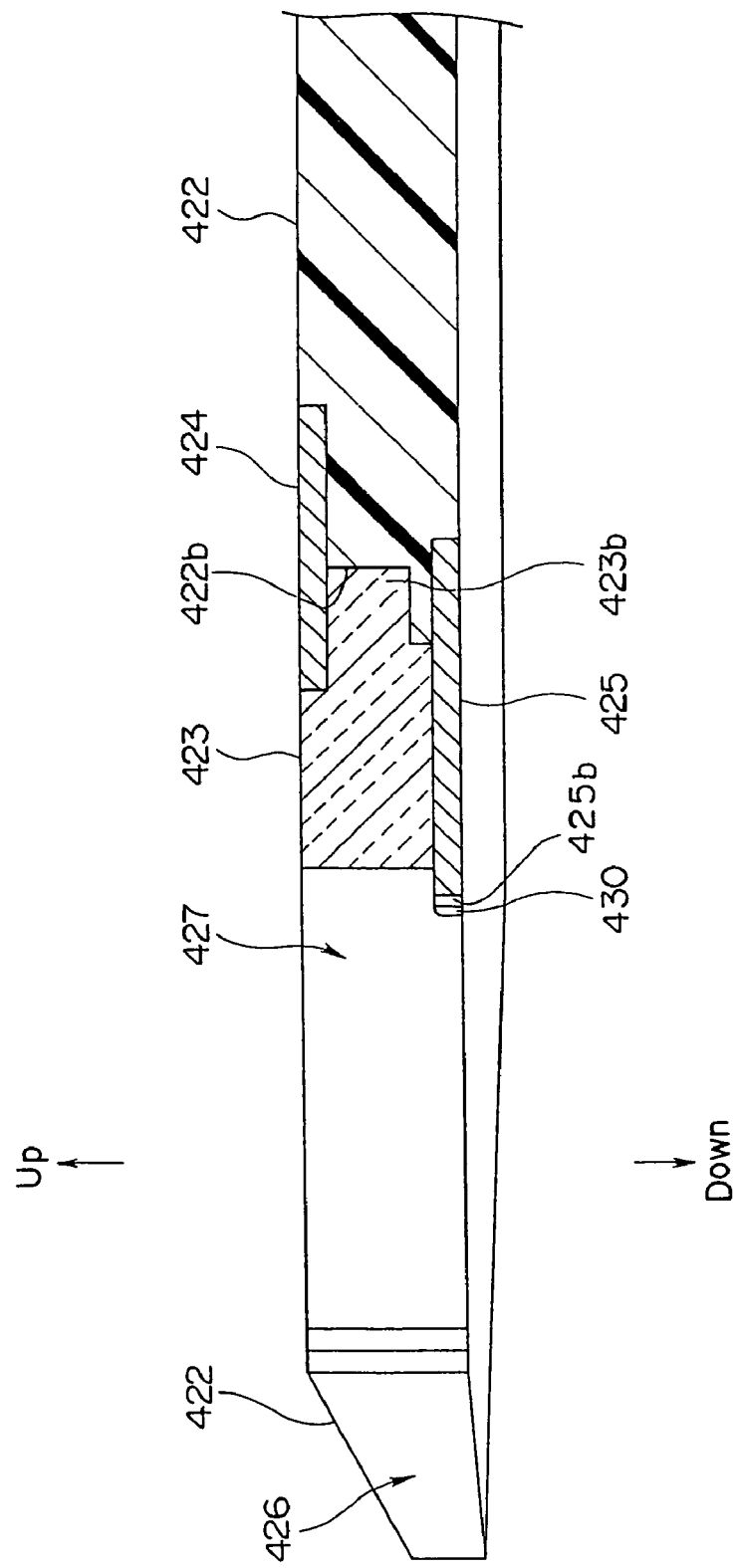
FIG. 23 is a sectional view of the bipolar cutter taken along the XXIII-XXIII line shown in FIG. 21 according to the first embodiment of the present invention.
Figure 24:
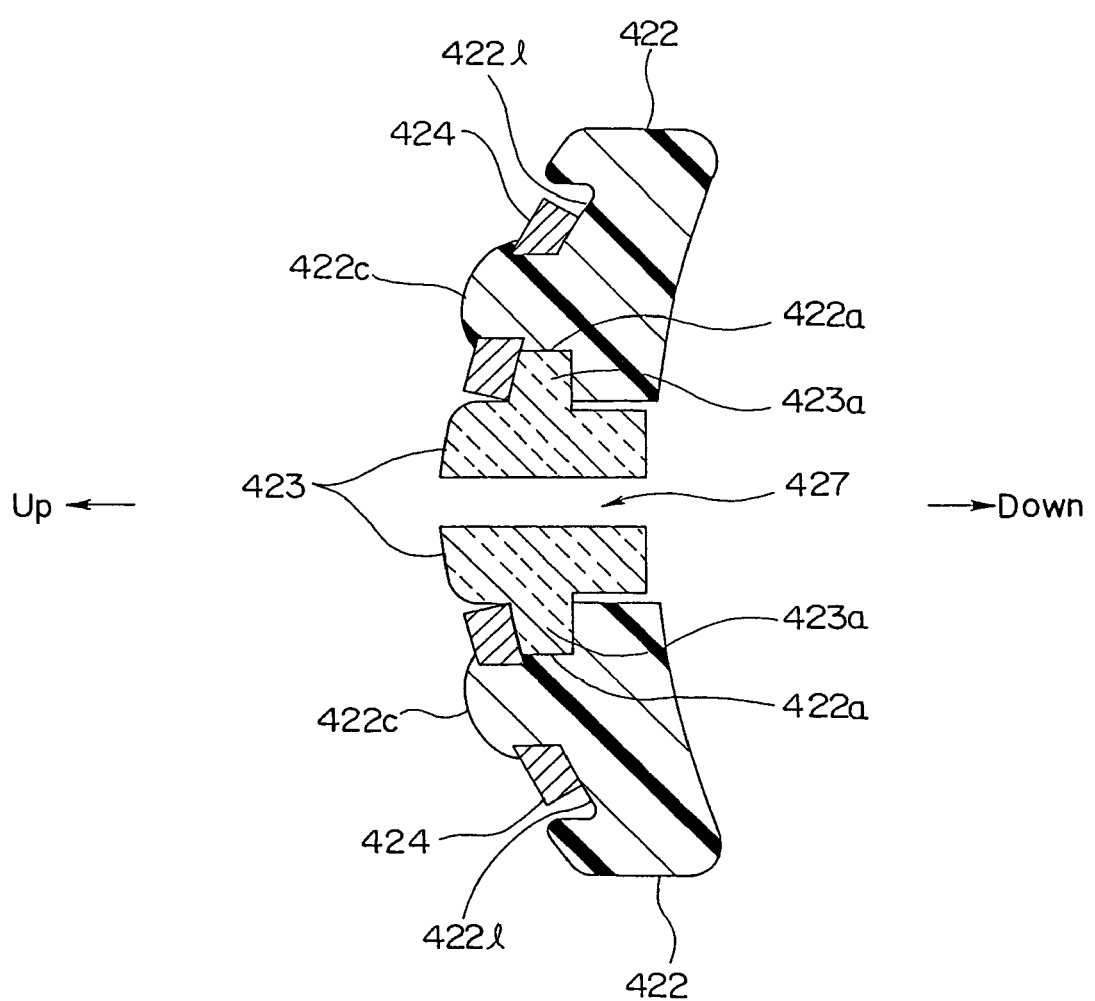
FIG. 24 is a sectional view of the bipolar cutter taken along the XXIV-XXIV line shown in FIG. 21 according to the first embodiment of the present invention.

FIG. 20 is an exploded perspective view of a distal-end part of the bipolar cutter 43, FIG. 21 is an illustration viewing the top surface of the bipolar cutter 43, FIG. 22 is an illustration viewing the undersurface of the bipolar cutter 43, FIG. 23 is a sectional view taken along the XXIII-XXIII line shown in FIG. 21, and FIG. 24 is a sectional view taken along the XXIV-XXIV line shown in FIG. 21.

As shown in FIG. 20 through FIG. 22, the bipolar cutter 43 has a cutter body 422 to be a body part made of a transparent insulating member, such as polycarbonate, a tissue holding part 423 made of ceramics, which is a nonmetallic inorganic substance used for an electrical insulating material, provided in substantially the center of the distal-end part, a pair of electrodes provided so as to sandwich at lease a part of the tissue holding part 423 in the direction upward and downward of the above endoscopic image, two lead wires 428 (voltage application side lead wire 428a, feedback side lead wire 428b), and a lead line cover 426a. The pair of electrodes is composed of a voltage application electrode 425 which is a first electrode, and one of electrodes in the bipolar, and a feedback electrode 424 which is a second electrode, and the other electrode of the electrodes in the bipolar. As shown in FIG. 23, the bipolar cutter 43 has a three-layered structure formed by an upper layer of the feedback electrode 424, the tissue holding part 423 and the cutter body 422, and the voltage application electrode 425. That is, at a part of the distal-end side of the cutter body 422, the feedback electrode 424 is the upper layer, the voltage application electrode 425 is the lower layer, and the tissue holding part 423 is provided between the feedback electrode 424 and the voltage application electrode 425. Thus, in order from the upper layer of the cutter body 422, the feedback electrode 424, the tissue holding part 423, and the voltage application electrode 425 are arranged as the three-layered structure. The feedback electrode 424 and the voltage application electrode 425 are not arranged on the same surface, but arranged to be opposite in upward and downward direction so as to hold the tissue holding part 423. For the sake of simplicity, in the first embodiment, it is determined that the side of a tissue (blood vessel) to be extracted (the side of the blood vessel holding base 411) is upward, and the side of a tissue to remain in the body is downward. That is, the voltage application electrode 425 is arranged at the lower side (the side of the blood vessel which is the tissue to be extracted) and the feedback electrode 424 is arranged at the upper side (the side of the tissue to remain in the body), respectively.

Again, returning to FIG. 20, to the cutter body 422, a fitting part 435 in which the tissue holding part 423 is fitted, a groove part 422j in which the lead wire 428a of the voltage application side and the lead wire 428b of the feedback electrode side are arranged respectively in an insulated state, and the lead wire cover 426a is fitted, and a concave part 422I on which the feedback electrode 424 is arranged, are provided. At the bottom surface of the groove part 422j, two long grooves are formed through the entire length of the groove part 422j to retain the insulated state between the lead wire 428a of the voltage application side and the lead wire 428b of the feedback side.

The fitting part 435 is composed of a first groove part 435a of a v-shaped groove 426 side and a second groove part 435b formed in substantially cylindrical shape at the proximal end side. On the inner circumference where the fitting part 435 of the cutter body 422 is formed, a fitting groove 422a to be an inward flange is formed, and on the position corresponding to the proximal end of the tissue holding part 423, a concave groove part 422b for fitting is formed.

As shown in FIG. 21 and FIG. 22, in the groove in which the lead wire of the voltage application side of the groove part 422j is arranged, a insertion part 422e in which a lead wire connecting part 425c of the voltage application electrode 425 is inserted at the distal-end side, is provided. Accordingly, at the voltage application electrode 425 arranged at the undersurface side of the cutter body 422, the lead wire connecting part 425c is inserted into the insertion part 422e, and the end part of the lead wire connecting part 425c and the lead wire 428a of the voltage application side arranged on the upper surface of the groove part 422j become to be electrically connectable.

The cutter body 422 is formed in arc-shapedly curved shape at the cross-section of band-shaped board body (see FIG. 24) so as to fit the arc-shaped inner circumference of the notch 415 (see FIG. 10) of the harvester 41.

Further, at the distal-end side of the cutter body 422, a v-shaped groove 426 is formed. In the direction to the proximal end side of the v-shaped groove 426, the tissue holding part 423 having a slit groove 427, for example, having the width of the slit groove of 0.5 mm, is fitted.

The tissue holding part 423 is formed in substantially cylindrical shape at the proximal end part, and has a part 423A formed in substantially cylindrical shape toward the distal end and a substantially rectangular-shaped part 423B extending from the peripheral side surface (see FIG. 21). Further, the tissue holding part 423 has convex parts 423a protruding from each side surface of the substantially rectangular-shaped part 423B opposite to the side of the slit groove 427, and a convex part 423b protruding from the outer circumference surface of the proximal end part of the substantially cylindrical part 423A toward the proximal end side. That is, the tissue holding part 423 is fitted in the cutter body 422 with the two convex parts 423a being fit into the fitting grooves 422a of the cutter body 422 (see FIG. 24) and with the convex part 423b being fit into the concave part 422b which is a fitting groove of the cutter body 422. The slit groove 427 is provided by being grooved in the longitudinal direction of the tissue holding part 423 from the distal-end central part of the substantially rectangular-shaped part 423B through the substantially central part of the substantially cylindrical part 423A. The high-heat-resistant ceramics structural material can be, for example, zirconia or alumina.

The feedback electrode 424, as shown in FIG. 21, is a metal plate having an arc-shaped part 424b formed by notching in substantially arc-shape at a boundary on the upper surface between the cutter body 422 and the tissue holding part 423, that is, parts substantially along the respective boundary, and a notch 424c formed spaced apart by a predetermined distance so as to hold the slit groove 427 at a part corresponding to the substantially rectangular-shaped part 423B of the tissue holding part 423. Further, along the upper surface of the tissue holding part 423, the feedback electrode 424 is formed in curved shape at the cross-section (see FIG. 24). Moreover, the feedback electrode 424 has a lead wire connecting part 424e electrically connected to a feedback side lead wire at the proximal end part by welding and a protruding part 424f juxtaposed with the lead wire connecting part 424e and fitted and held in the groove part 422j of the cutter body 422.

Further, the lead wire connecting part 424e and the protruding part 424f are bent down below substantially at a right angle respectively, further, bent substantially at a right angle so as to extend toward the proximal end side. The lead wire connecting part 424e is longer in the extending length toward the proximal end side than the extending length of the protruding part 424f, and has an enough length for the welding connection to the feedback side lead wire 428b.

That is, to the feedback electrode 424, the feedback side lead wire 428b for returning a high-frequency current passed through the inside of the cutter body 422 along the longitudinal direction of the cutter body 422 is connected such that the feedback side lead wire 428b extends from the proximal end. The feedback side lead wire 428b is electrically connected to an external electric knife device 107.

The protruding part 424f is shorter in the extending length toward the proximal end side than the length from the proximal end of the concave part 422l of the cutter body 422 to the insertion part 422e of the groove part 422j. Thus, the insulation is retained with the protruding part 424f not being contacted with the lead wire connecting part 425c of the voltage application electrode 425 and the voltage application side lead wire 428a, and the insulation between the feedback electrode 424 and the voltage application electrode 425 is also held. That is, the voltage application side lead wire 428a and the feedback side lead wire 428b are respectively arranged in parallel in two long grooves formed on the undersurface of the groove part 422j of the cutter body 422 so as to be isolated, and electrically connected to the external electric knife device 107 (see FIG. 7).

Further, here, four opening parts 424a, that is, two opening parts 424a are pierced on the distal-end side and the proximal end side respectively. The feedback electrode 424 is fixed to the cutter body 422 after fastening parts 422c (see FIG. 24) protruding from the upper surface of the cutter body 422 are inserted into the four opening parts 424a respectively and the fastening parts 422c are fused, and coagulated in flange shape. In the feedback electrodes 424, the opening parts 424a are not limited to four openings arranged for each two opening parts 424a on the distal-end side and the proximal end side, the arrangement and the number of the opening parts 424a can be varied so as to retain the strength of the fixation of the feedback electrode 424 to the cutter body 422.

Thus structured arc-shaped part 424b of the feedback electrode 424 positions on the surface of the tissue holding part 423 and by the periphery adjacent to the arc-shaped part 424b, by being superimposed with the tissue holding part 423, retains the substantially cylindrical part 423A of the tissue holding part 423. Further, the notched part 424c extendedly provided at the substantially central part of the distal-end side of the feedback electrode 424 is separated apart by a predetermined distance in the width direction of the slit groove 427 of the tissue holding part 423, and along the slit groove 427, extendedly provided in a state separated from the slit groove 427 by a substantially equal distance. The periphery adjacent to the notched part 424c of the feedback electrode 424, by being superimposed with the tissue holding part 423, retains the substantially rectangular-part 423B of the tissue holding part 423. Thus, the tissue holding part 423 is held by the feedback electrode 424 and prevented from being fell off the cutter body.

The tissue holding part 423 made of ceramics is difficult to fix to the cutter body 422 made of a different material, such as a synthetic resin, for example, polycarbonate. Accordingly, in the first embodiment, as described above, it is constructed that, by having a part where the arc-shaped part 424b of the feedback electrode 424 is superimposed with the tissue holding part 423, the tissue holding part 423 is held by the cutter body 422. However, for further ensuring the fixation of the tissue holding part 423 by being held by the feedback electrode 424 and preventing the tissue holding part 423 from falling off the cutter body 422, a modification will be described below.

That is, the fixing means of the feedback electrode 424 to the cutter body 422 for preventing the tissue holding part 423 from falling off the cutter body 422 is not limited to the fixing means that the fastening parts 422c are inserted into the opening parts 424a of the feedback electrode 424 and after the fastening parts are fused, coagulated in flange-shape as described above, it may be, for example, a structure shown in FIG. 25 through FIG. 38.

Figure 25:
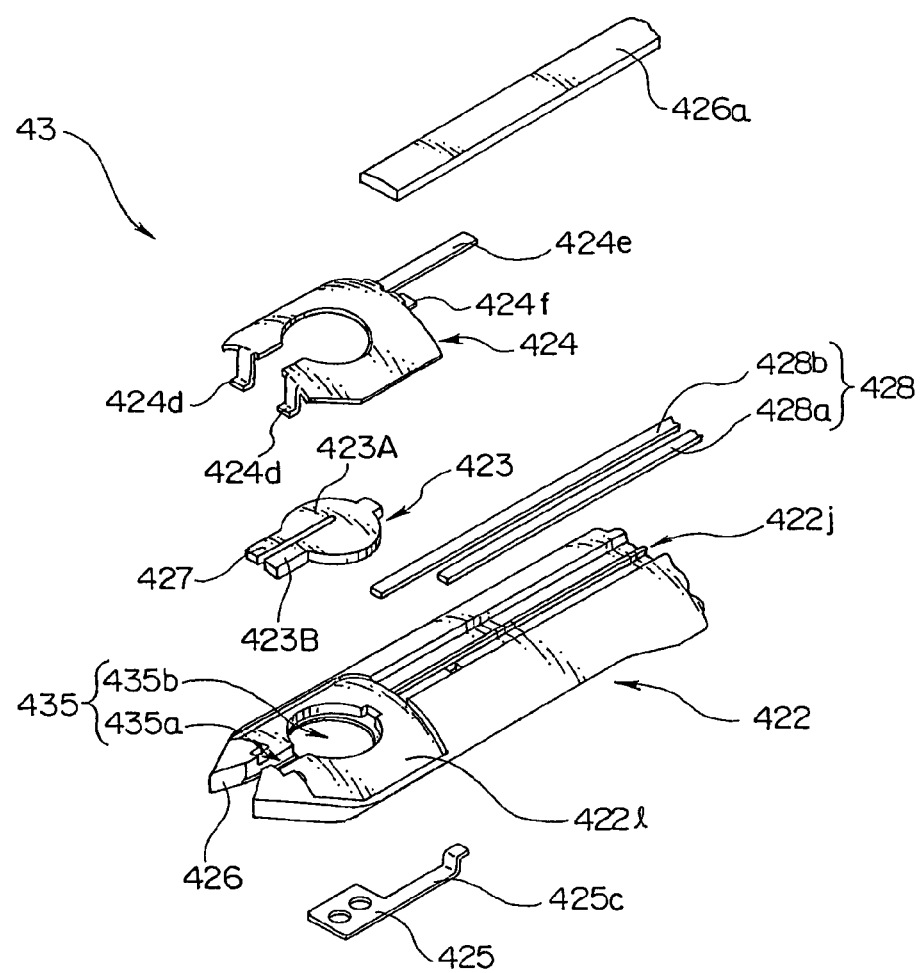
FIG. 25 is an exploded perspective view of a distal-end part of a bipolar cutter having a fixing means according to a first modification of the first embodiment.
Figure 28:
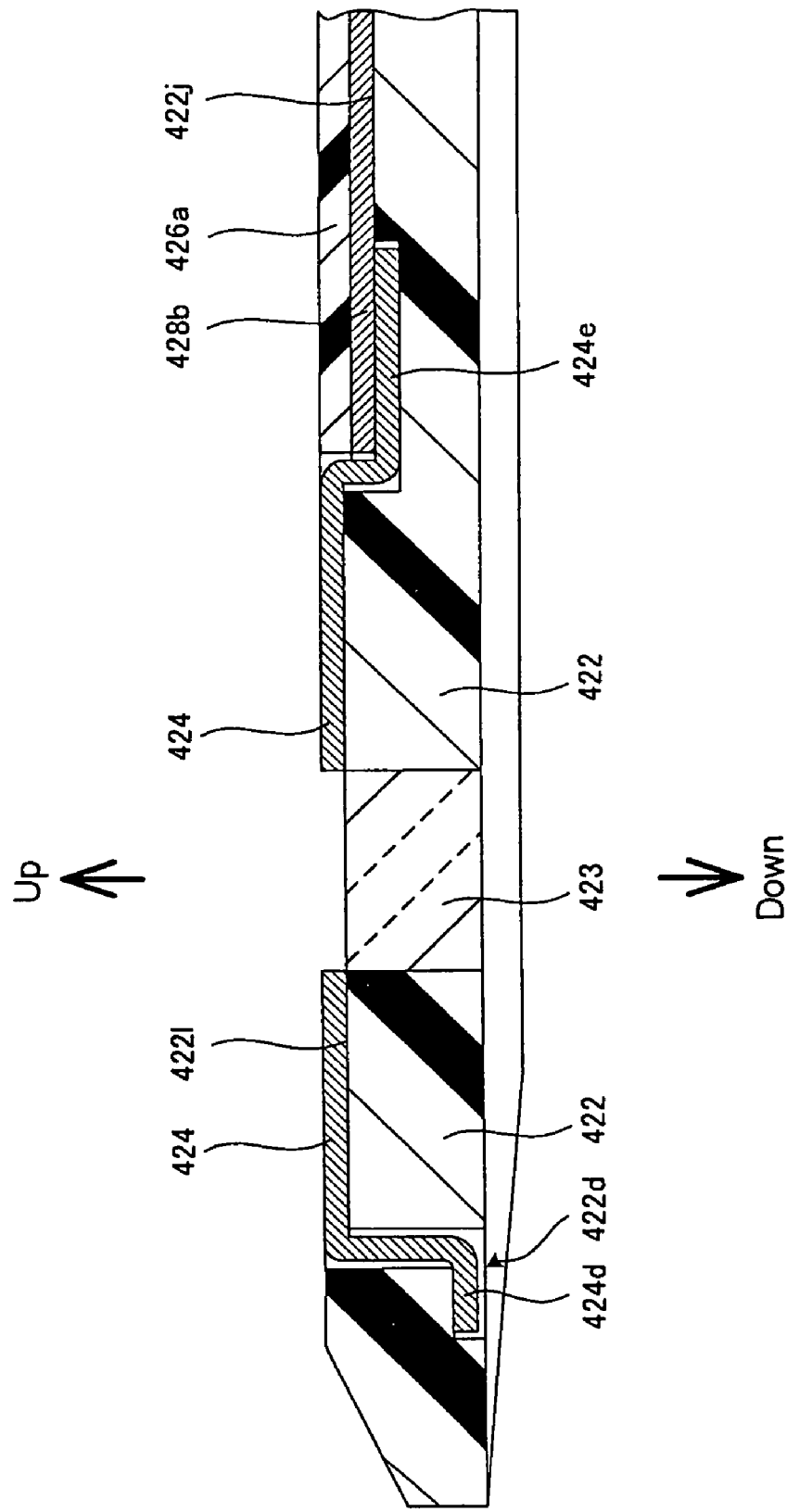
FIG. 28 is a sectional view of the bipolar cutter taken along the XXVIII-XXVIII line shown in FIG. 26 according to the first modification of the first embodiment.
Figure 29:
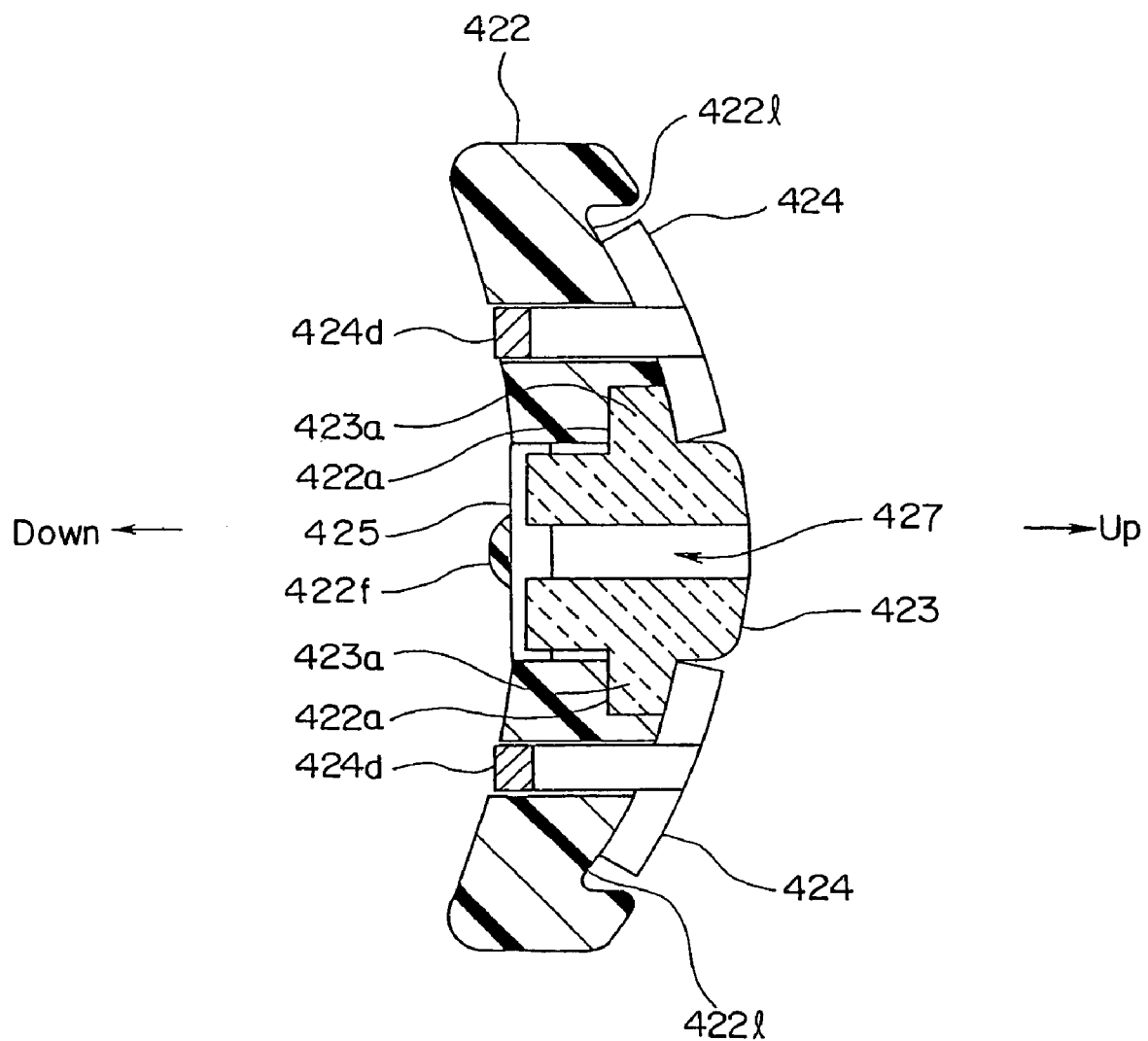
FIG. 29 is a sectional view of the bipolar cutter taken along the XXIX-XXIX line shown in FIG. 26 according to the first modification of the first embodiment.
Figure 30:
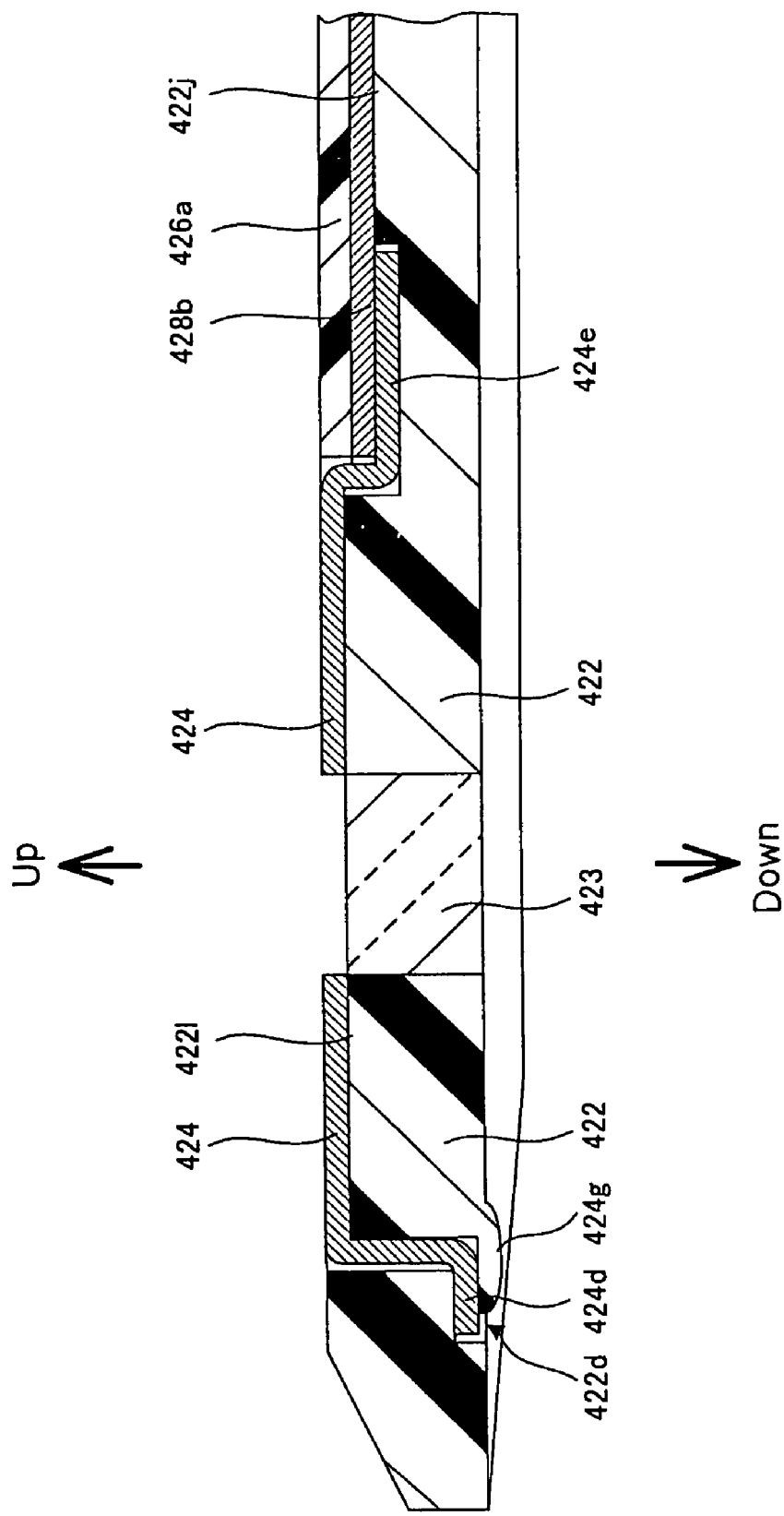
FIG. 30 is an illustration for explaining a caulking part according to the first modification of the first embodiment.

First, a first modification, which is a fixing structure of the feedback electrode 424 to the cutter body 422, will be described with reference to FIG. 25 through FIG. 33. FIG. 25 is an exploded perspective view of a distal-end part of the bipolar cutter 43, FIG. 26 is an illustration viewing the top surface of the bipolar cutter 43, FIG. 27 is an illustration viewing the undersurface of the bipolar cutter 42, FIG. 28 is a sectional view of the bipolar cutter 43 taken along the XXVIII-XXVIII line shown in FIG. 26, and FIG. 29 is a sectional view of the bipolar cutter 43 taken along the XXIX-XXIX line shown in FIG. 26.

As shown in FIG. 25, in the feedback electrode 424 in the first modification, two hook-shaped locking parts 424d are provided at the distal-end part. These two locking parts 424d are respectively being bent substantially at a right angle down below the feedback electrode 424, and the distal-end parts are further bent substantially at a right angle so as to extend forward.

Figure 26:
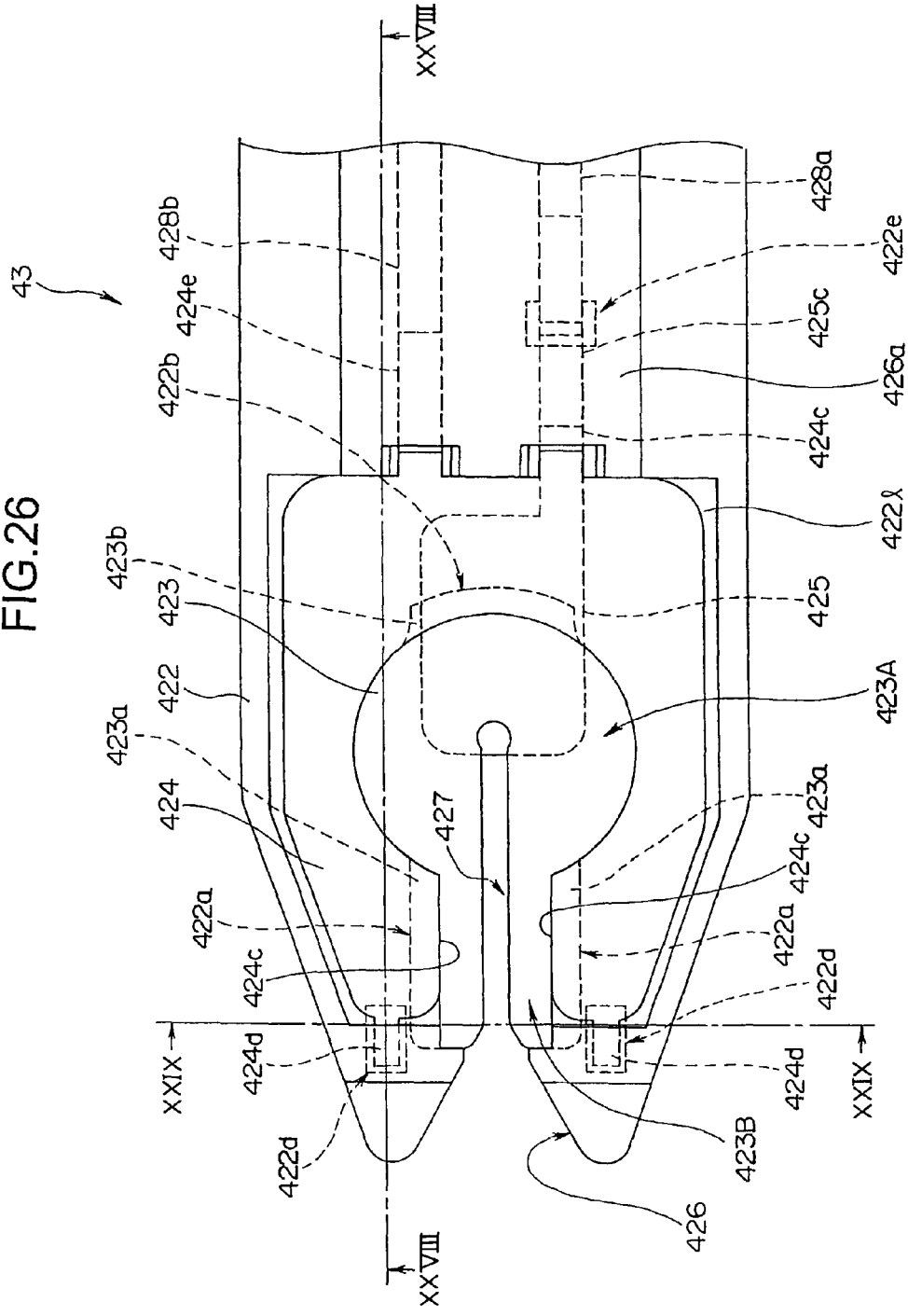
FIG. 26 is an illustration of the top surface of the bipolar cutter according to the first modification of the first embodiment.
Figure 27:
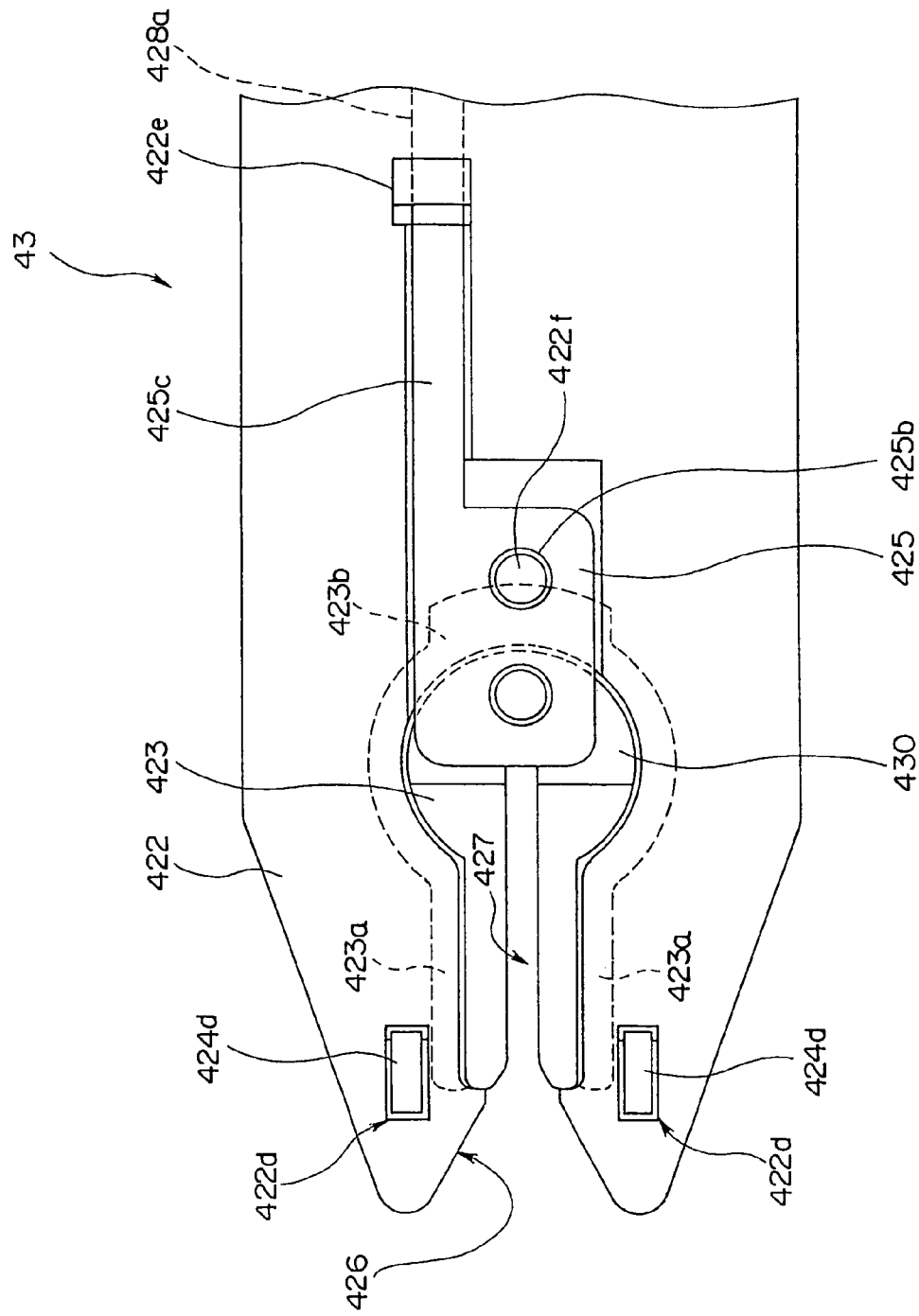
FIG. 27 is an illustration of the undersurface of the bipolar cutter according to the first modification of the first embodiment.

Further, as shown in FIG. 26 and FIG. 27, at the distal-end part of the concave part 4221 of the cutter body 422, two locking opening parts 422d corresponding to the two locking parts 424d of the feedback electrode 424 are provided.

More particularly, with the two locking parts 424d being inserted into the two locking opening parts 422d of the cutter body 422 respectively, the feedback electrode 424 is arranged on the concave part 4221 of the cutter body 422. And the lead wire connecting part 424e of the feedback electrode 424 is welded and connected to the distal-end part of the feedback side lead wire 428b by soldering or the like. The feedback side lead wire 428b is arranged in the long groove where the voltage application side lead wire 428a provided on the undersurface of the groove part 422j of the cutter body 422 is not arranged.

The feedback electrode 424 is held such that the locking parts 424d are hooked on the locking opening parts 422d of the cutter body 422, and the lead wire connecting part 424e and the protruding part 424f are sandwiched by the undersurface distal-end part of the lead wire cover 426a and the upper surface distal-end part of the groove part 422j of the cutter body 422. Accordingly, the feedback electrode 424 is strongly fixed to the cutter body 422 by being supported with the four parts; the two locking parts 424d, the lead wire connecting part 424e and the protruding part 424f.

As shown in FIG. 29, after the locking parts 424d of the feedback electrode 424 are inserted into the locking opening parts 422d of the cutter body 422, a caulking part 422g for sealing a part or all of the locking opening parts 422d from the undersurface side by thermal caulking may be provided. By providing the caulking part 422g on the undersurface of the locking opening parts 422d, the locking parts 424d are further strongly fixed to the locking opening parts 422d of the cutter body, and the fixation of the feedback electrode 424 to the cutter body 422 is further enhanced.

Accordingly, in the tissue holding part 423, as described above, each of the convex part 423a and the convex part 423b is contacted and held with the concave part 422b for fitting of the cutter body 422 and the fitting groove 422a respectively, further, each the upper surfaces of the convex part 423a and the convex part 423b is covered with the feedback electrode 424. Accordingly, it is ensured that the tissue holding part 423 is fitted into the fitting part 435 of the cutter body 422 and fixed, as that the tissue holding part 423 is prevented from falling off the fitting part 435.

Now, a second modification, which is fixing means for fixing the feedback electrode 424 to the cutter body 422, will be described with reference to FIG. 31 to FIG. 33.

Figure 31:
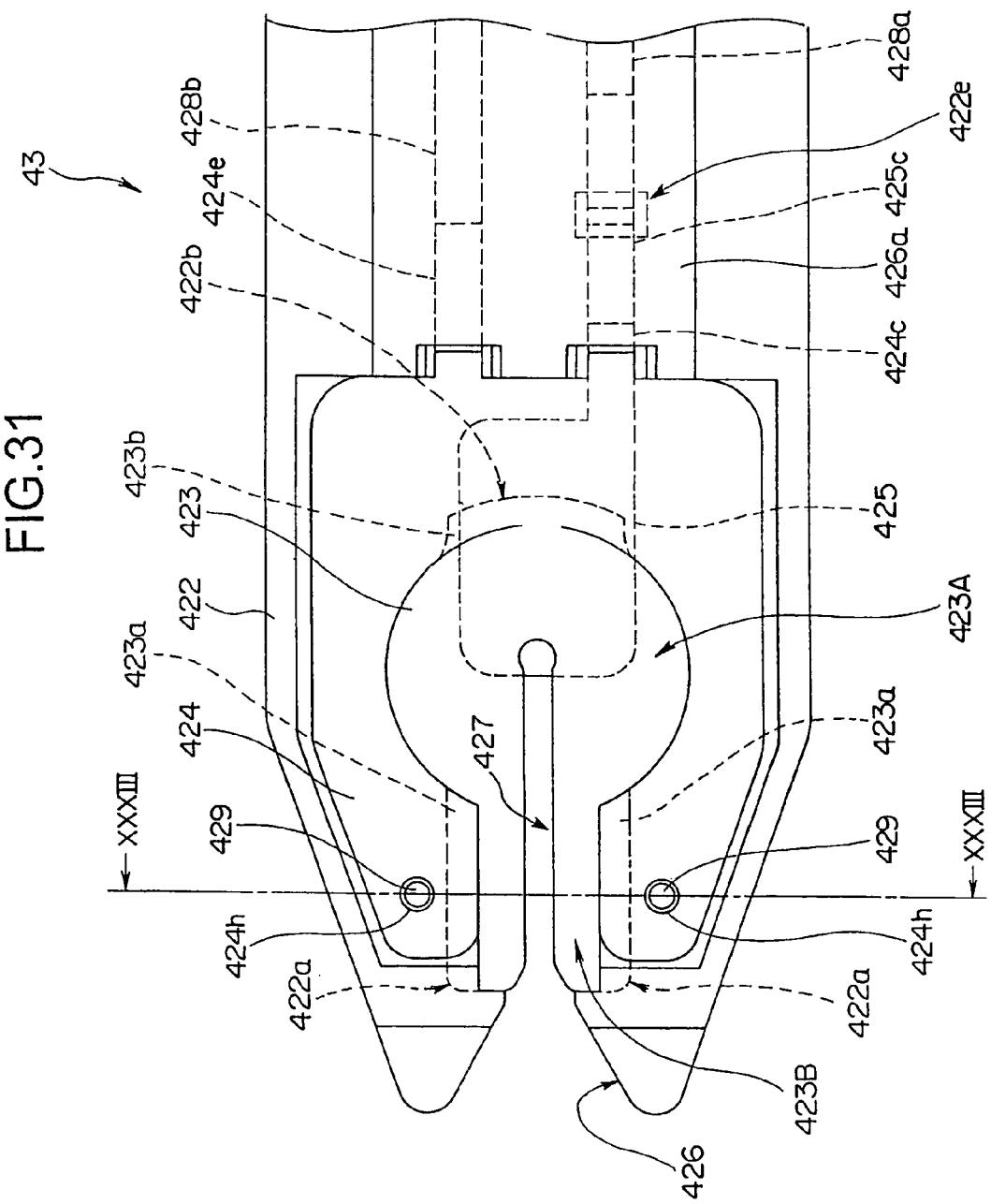
FIG. 31 is an illustration of a bipolar cutter having a fixing means viewed from the top surface according to a second modification of the first embodiment.
Figure 32:
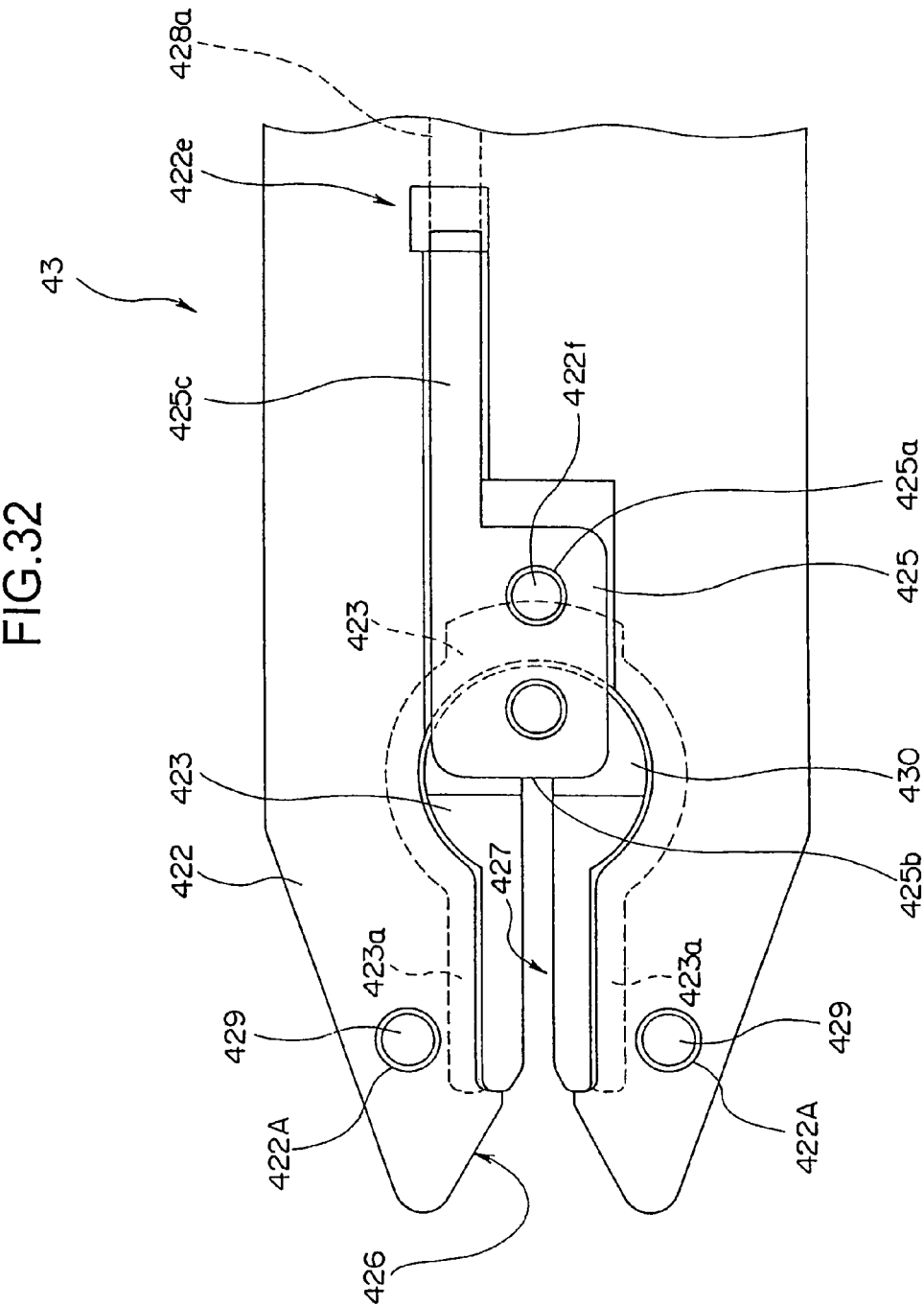
FIG. 32 is an illustration of the undersurface of the bipolar cutter according to the second modification of the first embodiment.
Figure 33:
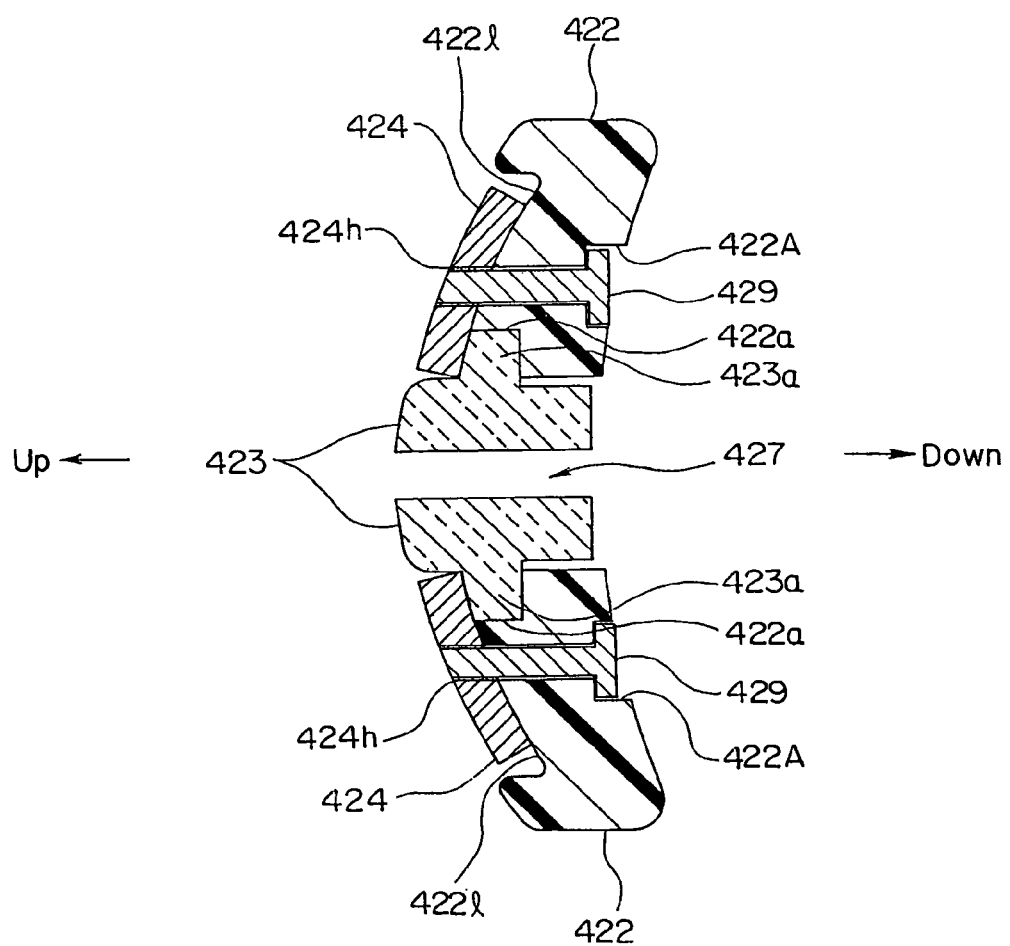
FIG. 33 is a sectional view of the bipolar cutter taken along the XXXIII-XXXIII line shown in FIG. 31 according to the second modification of the first embodiment.

FIG. 31 is an illustration viewing the top surface of a bipolar cutter 43, FIG. 32 is an illustration viewing the undersurface of the bipolar cutter 43, FIG. 33 is a sectional view of the bipolar cutter 43 taken along the XXXIII-XXXIII line shown in FIG. 31.

As shown in FIG. 31 through FIG. 33, the feedback electrode 424 is fixed by the cutter body 422 and a pin member 429 by welding such as laser welding, spot welding, brazing, or the like.

More particularly, at the distal-end side of the feedback electrode 424, two opening parts 424h are pierced. On the cutter body 422, pin openings 422A are arranged at positions corresponding to the two opening parts 424h of the feedback electrode 424 when the feedback electrode 424 is arranged to the concave part 4221 of the cutter body 422.

In the pin opening 422A, the diameter of the undersurface side of the cutter body 422 is large and at the middle part toward the upper surface of the cutter body 422, the diameter of the openings is small. To the pin opening 422A, a pin member 429 to which an outward flange is provided at one end is inserted form the other end side. The end where the outward flange of the pin member 429 is provided is a proximal end part and the end of the opposite side is a distal-end part.

In the feedback electrode 424 arranged on the concave part 4221 of the cutter body 422, the opening 424h is welded together and fixed with the distal-end part of the pin member 429 inserted into the pin opening 422A of the cutter body 422 by laser welding or the like.

Accordingly, the outward flange of the pin member 429 is contacted with the end surface part where the opening diameter becomes small at the middle of the pin opening part 422A of the cutter body 422, and with the distal-end part of the pin member 429 being welded together and fixed with the opening part 424h of the feedback electrode 424 by the welding, the feedback electrode 424 can be strongly fixed to the cutter body 422. Even in this state, the feedback electrode 424 is strongly fixed to the cutter body 422 such that the lead wire connecting part 424e and the protruding part 424f are being sandwiched by the undersurface distal-end part of the lead wire cover 426a and the upper surface distal-end part of the groove part 422j of the cutter body 422, and by being supported with the four parts; the two pin members 429, the lead line connecting part 424e and the protruding part 424f.

Now, a third modification, which is the fixing means for fixing the feedback electrode 424 to the cutter body 422, will be described with reference to FIG. 34 and FIG. 35.

Figure 34:
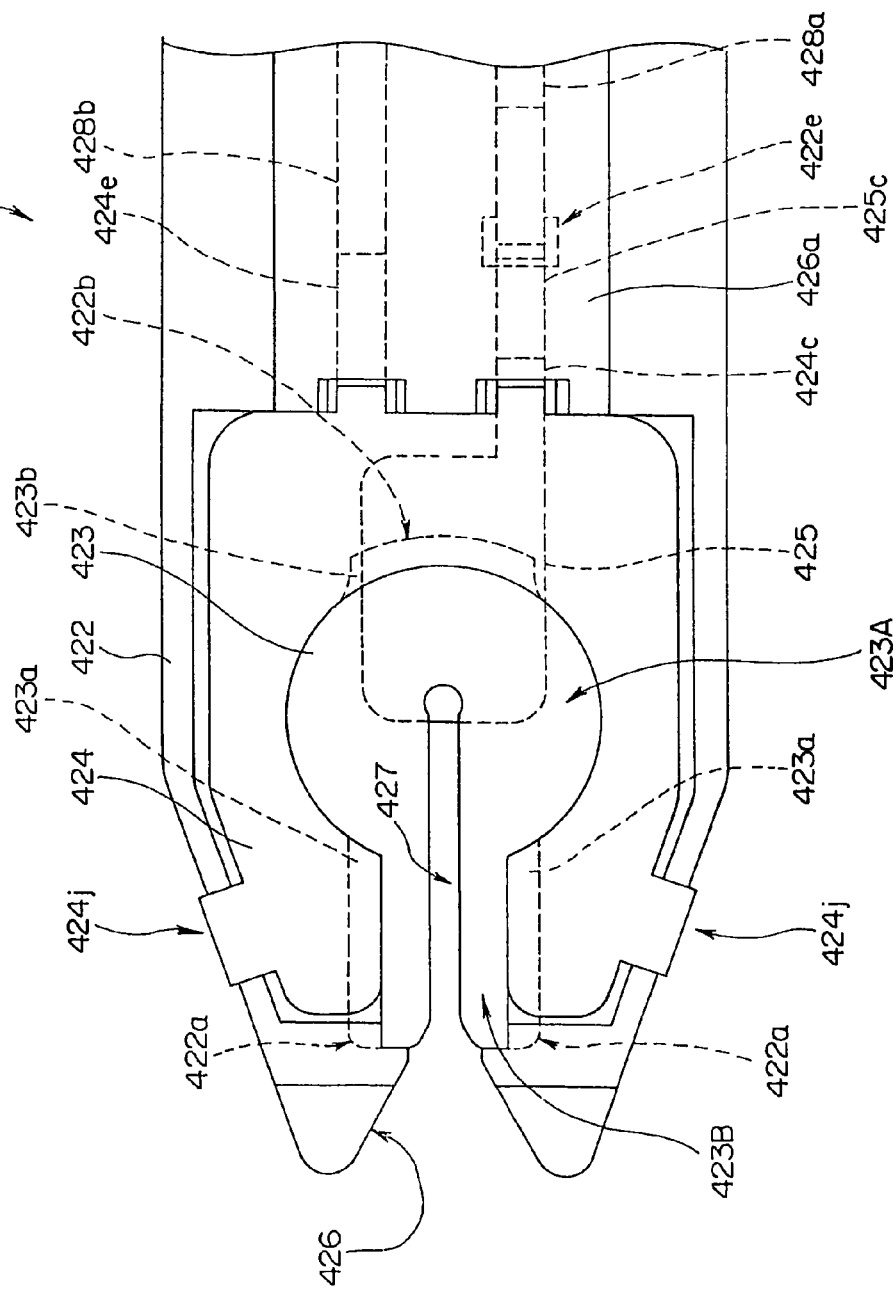
FIG. 34 is an illustration of a top surface of a bipolar cutter for explaining a fixing means according to a third modification of the first embodiment.
Figure 35:
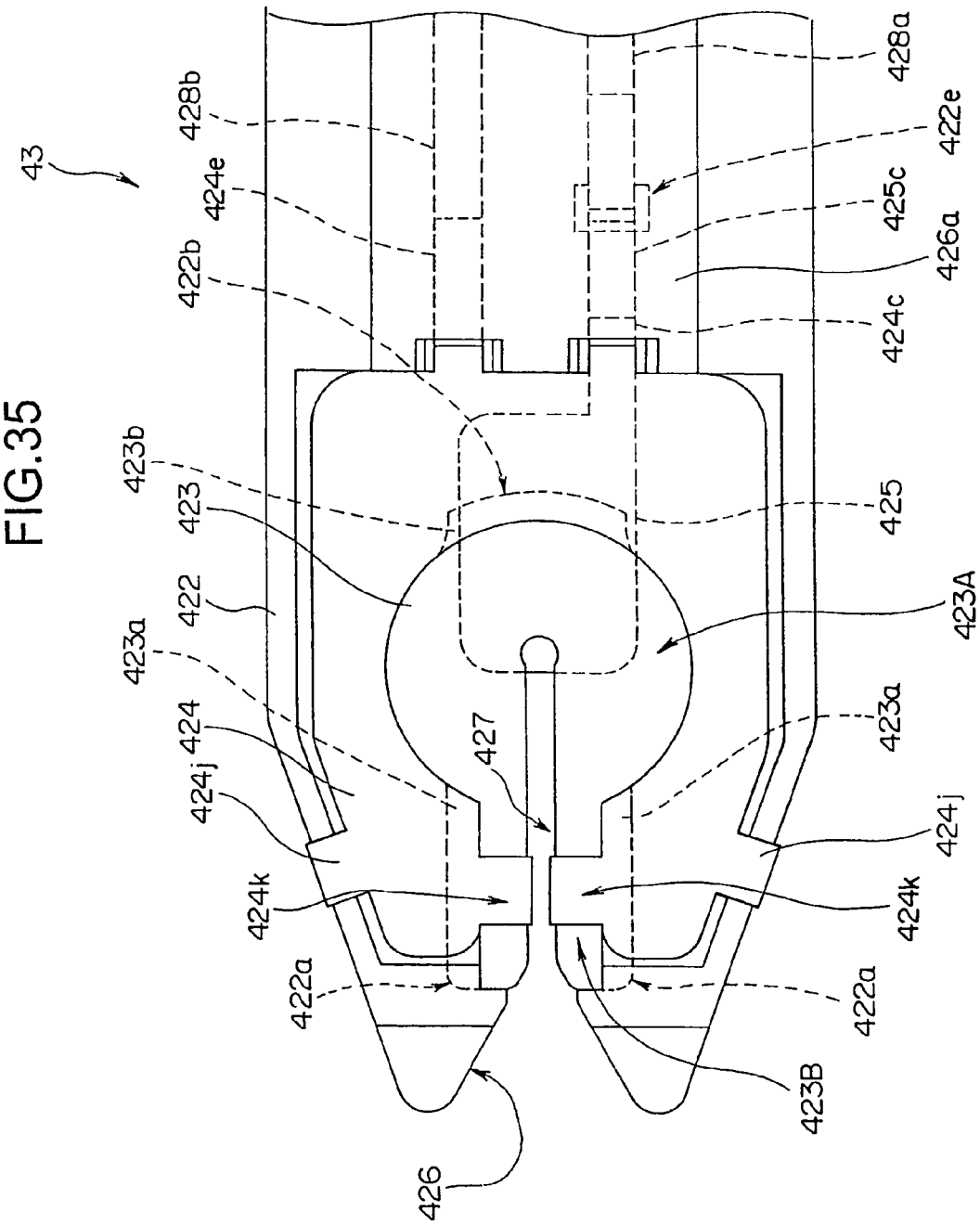
FIG. 35 is an illustration of a top surface of the bipolar cutter according to the third modification of the first embodiment.

FIG. 34 and FIG. 35 are illustrations viewing the top surface of the bipolar cutter 43.

As shown in FIG. 34, at the distal-end sides of the feedback electrode 424, the feedback electrode 424 has two turnup parts 424j protruding toward each outward direction. These two turnup parts 424j are folded back to the undersurface of the cutter body 422 so as to roll each outside part of the distal-end sides of the cutter body 422 respectively. Thus, it can be possible to fix the feedback electrode 424 to the cutter body 422.

Moreover, as shown in FIG. 35, at the distal-end side of the feedback electrode 424, turnup parts 424k protruding toward each inward direction are further provided. These two turnup parts 424k are folded back to the undersurface of the tissue holding part 423 so as to roll each inside part of the distal-end sides of the tissue holding part 423 along the slit groove 427 respectively. Thus, it can be possible to further strongly fix the feedback electrode 424 to the cutter body 422.

Then, a fourth modification, which is fixing means for fixing the feedback electrode 424 to the cutter body 422, will be described with reference to FIG. 36 through FIG. 38.

Figure 36:
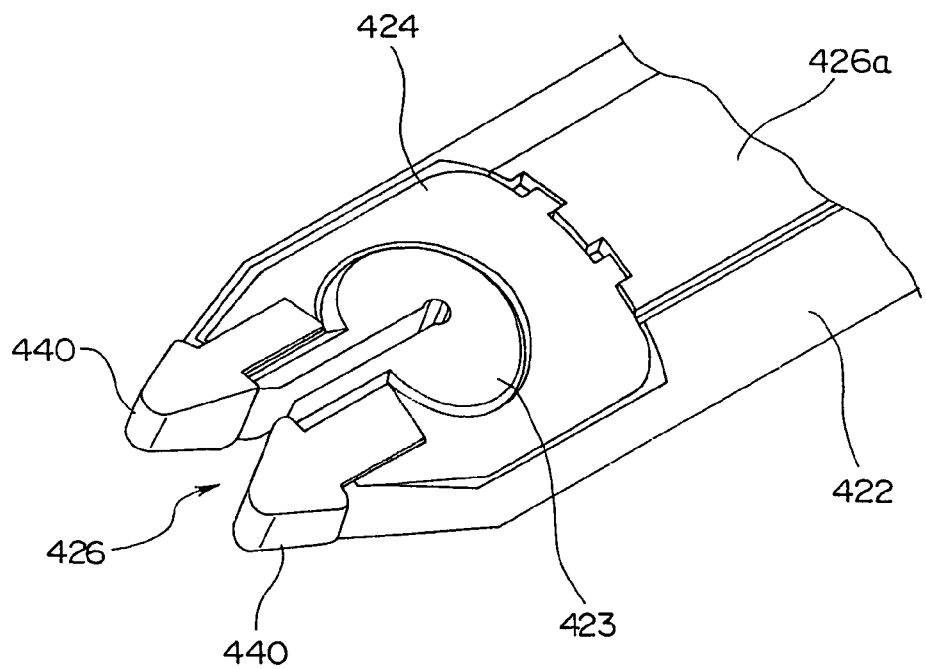
FIG. 36 is an illustration of a top surface of a bipolar cutter to explain a fixing means according to a fourth modification of the first embodiment.
Figure 37:
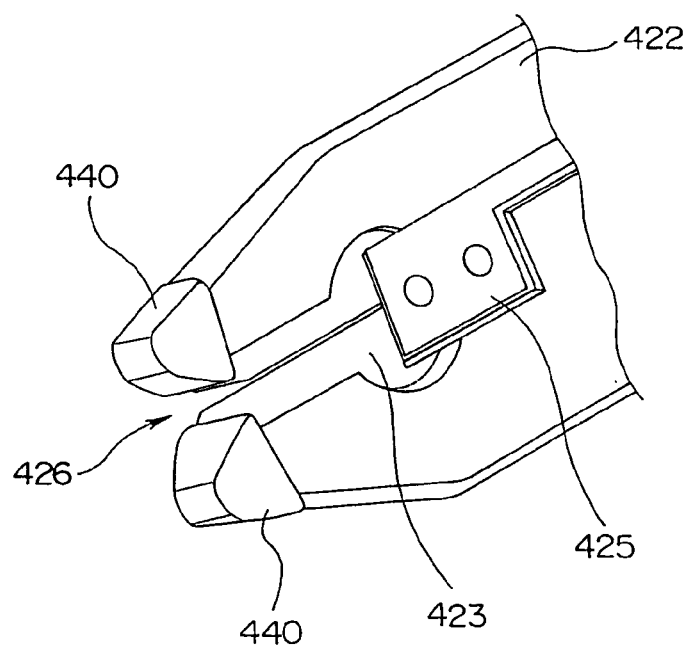
FIG. 37 is a perspective view of the bipolar cutter viewed from an undersurface according to the fourth modification of the first embodiment.

As shown in FIG. 36 and FIG. 37, on two protruding parts protruding forward at the distal-end part of the cutter body 422 in which a v-shaped groove 426 is formed, cup members 440 made of a metal (for example, stainless steel), a resin, or the like, are fixed respectively. In other wards, the cup members 440 are fixed to the cutter body 422 so as to cover the two protruding parts of the cutter body 422.

Figure 38:
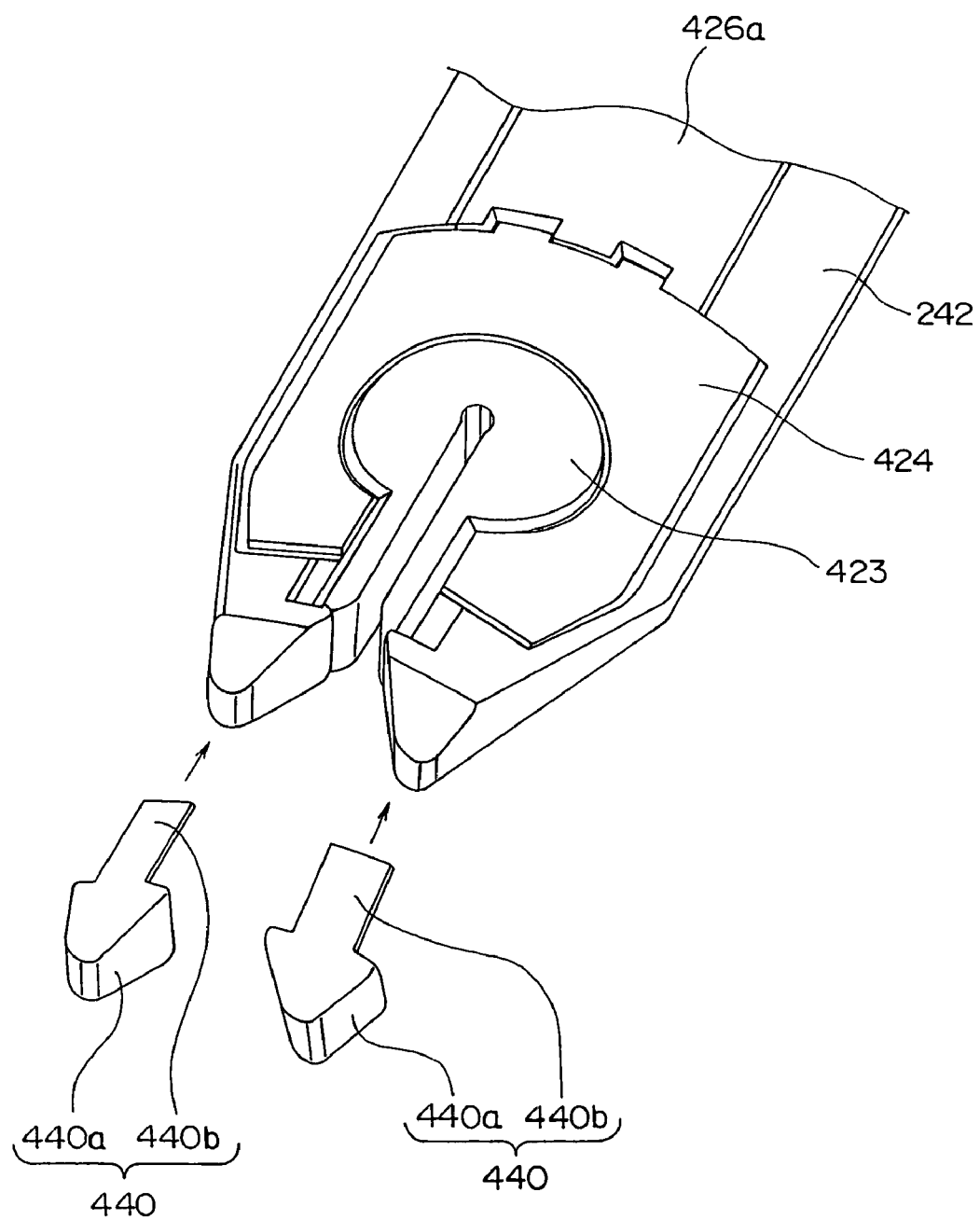
FIG. 38 is a perspective view of the bipolar cutter viewed from a top surface to explain a cup to be attached to a distal-end part of the cutter body according to the fourth modification of the first embodiment.

These two cup members 440, as shown in FIG. 38, have cup parts 440a having openings substantially the same shape as the protruding parts of the cutter body 422 in insides of the distal-end sides, and holding parts 440b extending backward from the proximal end of the cup parts 440a on the same surface as the upper surface of the cup parts 440a.

These two cup members 440 are engaged with the protruding parts of the cutter body 422 respectively so that the holding parts 440b hold the distal-end side upper surface of the feedback electrode 424. When the cup members 440 are made of a metal, the holding parts 440b and the feedback electrode 424 are welded together. On the other hand, when the cup members 440 are made of a resin, the cup parts 440a and the protruding parts of the cutter body 422 are adhered. In this case, the cup parts 440a and the protruding parts of the cutter body 422 are formed so that a mechanical fitting can be performed. Further, in this case, the holding parts 440b and the feedback electrode 424 may be additionally adhered.

As described above, since each holding part 440b of the two cup members presses and holds the distal-end side upper surface of the feedback electrode 424 toward the side of the cutter body 422, the feedback electrode 424 can be strongly fixed to the cutter body 422.

Also in each above-described fixing means for fixing the feedback electrode 424 to the cutter body 422, the arc-shaped part 424b of the feedback electrode 424 positions on the surface of the tissue holding part 423, and with the periphery adjacent to the arc-shaped part 424b being superimposed with the tissue holding part 423, the tissue holding part 423 used for the bipolar cutter 43 is held by the feedback electrode 424 and prevented from falling off the cutter body 422. That is, by the feedback electrode 424, it can be possible to ensure to hold the tissue holding part 423 formed of ceramics to the cutter body 422 made of a different material, such as a synthetic resin, for example, polycarbonate.

Returning to FIG. 21, the voltage application electrode 425 is a metal plate of substantially rectangular shape arranged at the undersurface side of the cutter body 422 and the tissue holding part 423 and having a cutting part 425b for cutting the branch 11A by applying a high-frequency current to the distal-end part in contact with the branch 11A. The distal-end part of the voltage application electrode 425 is placed at substantially central part of the cylinder part of the tissue holding part 423 so that the side of the proximal end of the slit groove 427 of the tissue holding part 423 is covered over. On the undersurface of the tissue holding part 423, a step part 430 which is notched toward the proximal end side is formed for positioning the distal-end part of the voltage application electrode 425.

From the voltage application electrode 425, the above-mentioned lead wire connecting part 425c eclectically connected with the voltage application side lead wire 428a by welding extends toward the proximal end side. In the lead wire connecting part 425c, the end part of the extending direction is bent upward substantially at a right angle and further, the end part is bent substantially at a right angle toward the extending direction side.

More particularly, the lead wire connecting part 425c of the voltage application electrode 425 is inserted into the insertion part 422e of the cutter body 422, and the fastening part 422f of the cutter body 422 is inserted into the opening part 425a of the voltage application electrode 425. Then, the fastening part 422f of the cutter body 422 is formed as an outward flange by a thermal caulking, and the upper surface of the voltage application electrode 425 is fixed to the cutter body 422 such that the upper surface of the voltage application electrode 425 faces the undersurface of the cutter body 422 and the surface of the step part 430 of the tissue holding part 423. That is, as well as the feedback electrode 424, the voltage application electrode 425 is fixed to the cutter body 422 such that the fastening part 422c protruding from the undersurface of the cutter body 422 is inserted into the opening part 425a, and the fastening part 422c is fused and coagulated in flange shape.

Then, the lead wire connecting part 425c of the voltage application electrode 425 is welded and connected with the distal-end part of the voltage application side lead wire 428a by brazing or the like. The voltage application side lead wire 428a is arranged in one groove of the undersurface of the groove part 422j of the cutter body 422.

Further, the lead wire cover 426a is fit in the groove part 422j of the cutter body 422 with a resin adhesive or the like in the state that the insulation between the voltage application side lead wire 428a and the feedback side lead wire 428b is retained.

As described above, the bipolar cutter 43 is assembled in the three-layered structure in which the upper layer is the feedback electrode 424, the middle layer is the tissue holding part 423 and the cutter body 422, and the lower layer is the voltage application electrode 425.

The cutting part 425b of the voltage application electrode 425 positions at substantially center of the arc part of the arc-shaped part 424b of the feedback electrode 424, and arranged on the axis substantially orthogonal to the long axis and the short axis of the cutter body 422. That is, each arranging position of the feedback electrode 424 and the voltage application electrode 425 is determined such that a predetermined creepage distance at the tissue holding part 423 from the cutting part 425b to the arc-shaped part 424b is substantially equal.

In other wards, the feedback electrode 424 is, in order to keep the predetermined creepage distance at the tissue holding part 423 provided for electric strength, arranged such that the distance from the cutting part 425b of the voltage application electrode 425 which positions at the proximal end side of the slit groove 427 and the arc-shaped part 424b of the feedback electrode 424 is substantially equal. Further, the feedback electrode 424 is notched in substantially arc-shape as substantially centering the proximal end part of the slit groove 427, and the side surface of the feedback electrode 424 forms is the arc-shaped part 424b. That is, in order to keep the creepage distance between the feedback electrode 424 and the cutting part 425b of the voltage application electrode 425 arranged at the proximal end part of the slit groove 427, the arc-shaped part 424b is formed in the feedback electrode 424 such that the cutting part 425b is arranged at substantially the center of the arc of the arc-shaped part 424b.

Further, by forming the tissue holding part 423 with ceramics and forming the tissue holding part 423 in substantially cylindrical shape so as to correspond to the substantially arc-shaped part 424b of the feedback electrode 424 side, the heat generated at the cutting part 425b of the voltage application electrode 425 is transmitted substantially uniformly at the tissue holding part 423. In other wards, at the tissue holding part 423 arranged among the cutter body 422, the feedback electrode 424 and the voltage application electrode 425, the heat generated at the cutting part 425b of the voltage application electrode 425 radiates out, and at the vicinity of the cutting part 425b of the voltage application electrode 425, it can be possible to reduce a local high temperature. Accordingly, since the heat generated at the voltage application electrode 425 substantially uniformly radiates out through the tissue holding part 423, it can be possible to reduce the overheat of the cutter body 422 neighboring the tissue holding part 423 and the tissue holding part 423.

Further, the above-described arc-shaped part 424b of the feedback electrode 424 has a larger area than the cutting part 425b of the voltage application electrode 425 being exposed at the proximal end of the slit groove 427. Thus, the blood stanching ability can be enhanced. Moreover, as described above, in the first embodiment, by arranging the cutting part 425b of the voltage application electrode 425 at substantially the center of the arc of the arc-shaped part 424b of the feedback electrode 424, while sufficiently ensuring an area (the arc-shaped part 424b in the embodiment) of the part of the feedback electrode 424 which is most neighboring the cutting part 425b, the creepage distance between the area and the cutting part 425b can be retained substantially equal. Thus, by the structure, since it is possible to form the feedback electrode 424 to have a sufficiently large area with respect to the voltage application electrode 425 while ensuring the creepage distance of the cutting part 425b with respect to the feedback electrode 424, the blood stanching ability can be enhanced.

Now, the cutting of the branch 11A by the bipolar cutter 43 of the harvester 41 will be described with reference to FIG. 39 through FIG. 41.

Figure 39:
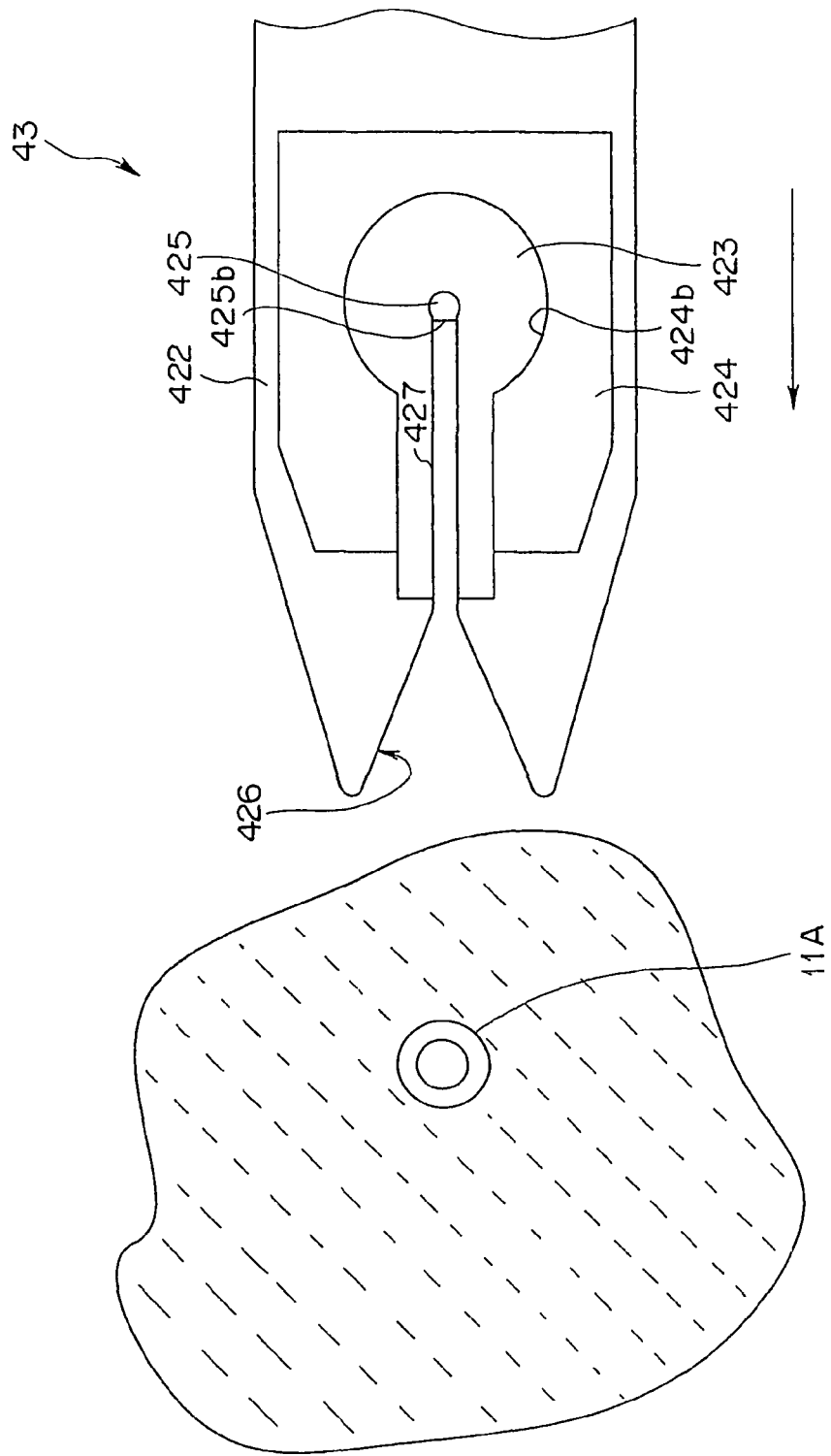
FIG. 39 is an illustration for explaining a cutting operation of a branch with the bipolar cutter according to the first embodiment of the present invention.
Figure 40:
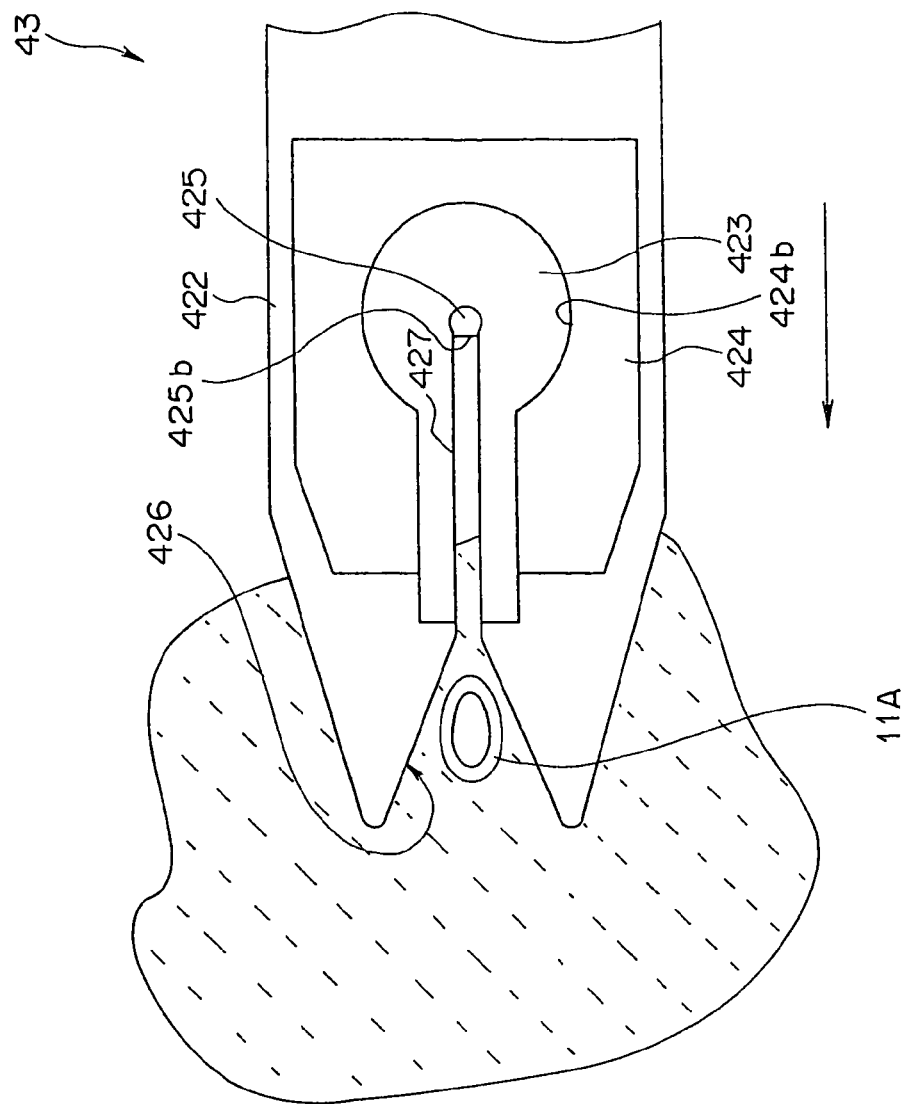
FIG. 40 is an illustration for explaining the cutting operation of the branch with the bipolar cutter according to the first embodiment of the present invention.
Figure 41:
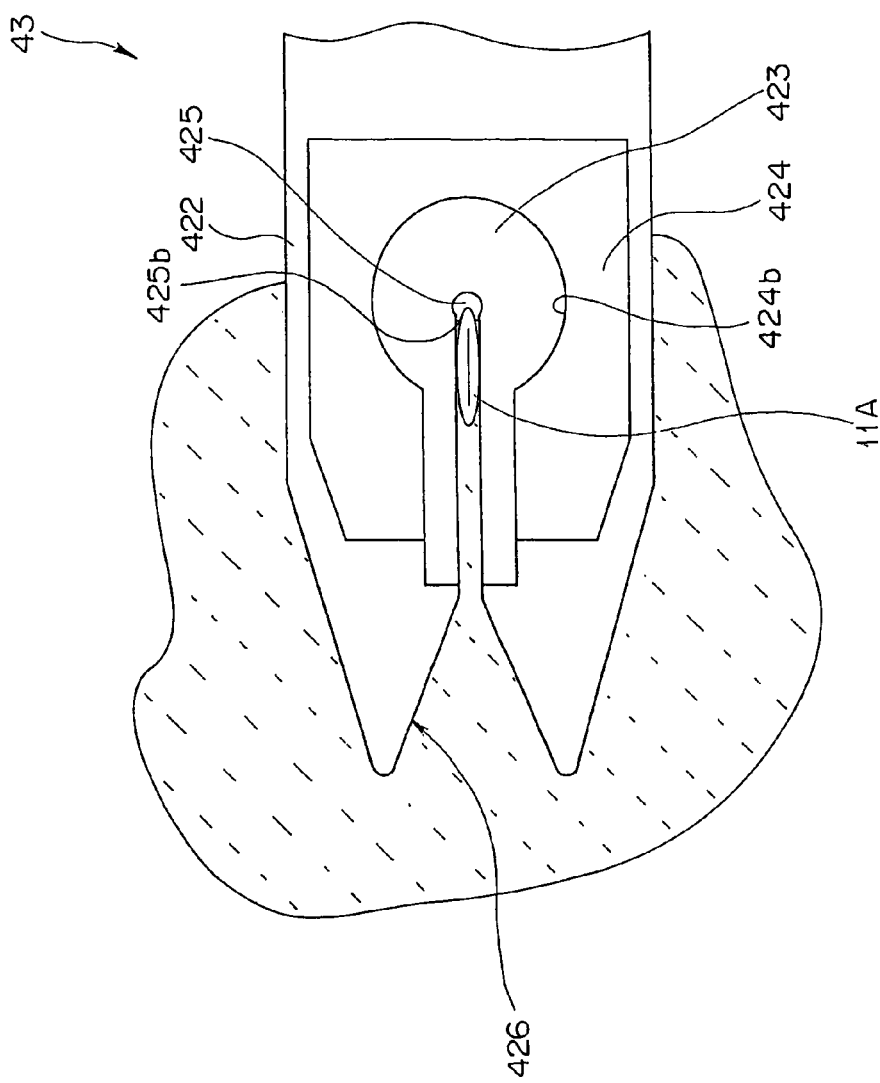
FIG. 41 is an illustration for explaining the cutting operation of the branch with the bipolar cutter according to the first embodiment of the present invention.

FIG. 39 through FIG. 41 are illustrations for explaining the cutting of the branch 11A by the bipolar cutter 43.

After peripheral tissues of the entire length of the blood vessel 11 are dissected (S4) by using the dissector 31, which is described in FIG. 1, the dissector 31 is pulled out of the trocar 21, the trocar 21 is being left, the harvester 41 is inserted, and cutting operation of the branch of the blood vessel 11 from the incision 16 through the ankle 14 is performed (S5).

As shown in FIG. 39, the operator moves forward the bipolar cutter 43 toward the branch 11A while confirming the endoscopic image. Then, while confirming the endoscopic image, the operator performs sliding operation of the bipolar cutter lever 401 of the harvester 41 in the direction that the bipolar cutter 43 moves forward so that the branch 11A enters in the v-shaped groove 426 of the cutter body 422.

Then, as shown in FIG. 40, the branch 11A is entered in the v-shaped groove 426. Further, as the bipolar cutter 43 is moved forward toward the branch 11A, the branch 11A is guided to the slit groove 427 of the tissue holding part 423 by the v-shaped groove 426, and pulled.

As shown in FIG. 41, as the bipolar cutter 43 is further moved forward, the branch 11A is guided into the slit groove 427 in a pressed manner. Then, the branch 11A is held in a compressed state in the slit groove 427. In this state, the operator confirms by the endoscopic image that the branch 11A is in contact with the cutting part 425b of the voltage application electrode 425, and applies a high-frequency current from the electric knife device 107. Then, the high-frequency current discharged form the cutting part 425b of the voltage application electrode 425 passes to the arc-shaped part 424b of the feedback electrode 424 through the surface of the tissue holding part 423. The branch 11A compressed in the slit groove 427 of the tissue holding part 423 is coagulated by heat applied from the part of the cutting part 425b contacting with the voltage application electrode 425 and cut.

Here, the heat generated by the high-frequency current discharged from the voltage application electrode 425 to the feedback electrode 424 concentrates in the vicinity of the voltage application electrode 425. However, by using the tissue holding part 423 made of ceramics which has high heat resistance for the part held between the voltage application electrode 425 and the feedback electrode 424, it can be possible to realize the structure excellent in high heat resistance.

Further, the branch 11A is made compressed by the slit groove 427 of the tissue holding part 423, and since the heat is applied in this state, the branch 11A is cut in further ensured blood stanching state.

Further, since the cutter body 422 of the bipolar cutter 43 is made of a synthetic resin such as polycarbonate, as compared to the cutter bodies entirely made of ceramics, the cutter body 422 is excellent in workability and less expensive.

As a result from the above, by using the bipolar cutter 43 of the harvester 41 which is the cutting means according to the first embodiment, with the tissue holding part 423 having durability, the voltage application electrode 425 and the feedback electrode 424, the operator can stanch and cut the branch 11A readily and in the further ensured state.

While the present invention has been described with reference to an exemplary embodiment, it is to be understood that the invention is not limited to the disclosed exemplary embodiment, it is possible to make various changes and modifications to the invention without departing from the spirit and scope of the claims.

What is claimed is:

1. An instrument for cutting a living tissue comprising:
   a cutter body having a distal end side and a proximal end side;
   a living tissue guiding groove for guiding the living tissue, the living tissue guiding groove being extended from the distal end side of the cutter body toward the proximal end side of the cutter body;
   a tissue holding part including an electrically insulating material being partially arranged in the living tissue guiding groove, the tissue holding part defining a slit groove which extends toward a proximal end side of the tissue holding part from a distal end side of the tissue holding part, has a distal end side and a proximal end side, has a substantially uniform groove width, and is configured to guide the living tissue from the living tissue guiding groove toward the proximal end side of the slit groove;
   a first electrode arranged on a first surface of the tissue holding part such that a part of a distal end of the first electrode is positioned on a proximal end side of the slit groove, the first electrode having a cutter configured to cut the living tissue guided from the living tissue guiding groove toward the proximal end side of the slit groove; and
   a second electrode arranged on a second surface of the tissue holding part opposite to the first surface of the tissue holding part on which the first electrode is arranged, and configured to hold a part of the tissue holding part with respect to the cutter body,
   wherein the first electrode, the tissue holding part and the second electrode are arranged on a distal end part of the cutter body so as to be superimposed in this order from the first surface toward the second surface of the tissue holding part.

2. The instrument for cutting a living tissue according to claim 1, wherein the tissue holding part is made of ceramics.

3. The instrument for cutting a living tissue according to claim 1, wherein
   the second electrode includes an arc-shaped part defining a substantially arc-shaped opening, and
   the first electrode is arranged with respect to the second electrode such that the cutter of the first electrode is arranged spaced apart from the center of the substantially arc-shaped opening on an axis substantially orthogonal to a longitudinal axis and a latitudinal axis of the cutter body via the tissue holding part, and that distances from the cutter of the first electrode to each part of the periphery of the substantially arc-shaped opening of the second electrode are substantially equal.

4. The instrument for cutting a living tissue according to claim 3, wherein the area of the second electrode is greater than the area of the cutting part of the first electrode positioned at the proximal end part of the slit groove.

5. The instrument for cutting a living tissue according to claim 4, wherein the second electrode includes a notched part which is connected to the arc-shaped part and is formed toward the distal end side of the second electrode, and
the notched part is formed in parallel to the slit groove formed to the tissue holding part and each part of the periphery of the notched part is spaced apart from the slit groove by a predetermined distance.

6. An instrument for cutting a living tissue comprising:
an insertion part to be inserted in a body, the insertion part having a longitudinal axis defining a distal end side and a proximal end side of the insertion part;
a holder arranged at a first outer circumference side of the distal end side of the insertion part, for holding the living tissue; and
a cutter arranged movably forward and backward in a direction of the longitudinal axis of the insertion part, for cutting the living tissue;
wherein the cutter comprises:
a cutter body arranged, with respect to the holder, at a second outer circumference side of the distal end side of the insertion part, with the center of the distal end side of the insertion part therebetween, and having a living tissue guiding groove for guiding the living tissue;
a pair of electrodes arranged on the distal end side of the cutter body; and
a tissue holding part made of an electrically insulating material, a part of the tissue holding part is arranged between the pair of electrodes, and on which a slit groove is formed such that the living tissue guiding groove is operatively connected to the slit groove to guide the living tissue into the slit groove,
wherein the pair of electrodes comprises:
a first electrode for applying a high-frequency current; and
a second electrode for returning the high-frequency current from the first electrode, and
wherein the pair of electrodes and the tissue holding part are arranged at a distal end part of the cutter body such that the first electrode, the tissue holding part, and the second electrode are superimposed in this order from the center of the distal end side of the insertion part toward the second outer circumference side.

7. The instrument for cutting a living tissue according to claim 6, wherein the insertion part has a channel for housing an endoscope in the insertion part.

8. The instrument for cutting a living tissue according to claim 6, further comprising an operating member for moving the cutter forward and backward in the direction of the longitudinal axis of the insertion part, relatively to the insertion part.

9. The instrument for cutting a living tissue according to claim 6, wherein
the first electrode is arranged on a first surface of the tissue holding part so that a part of a distal end of the first electrode is positioned at a proximal end part of the slit groove, and is configured to cut the living tissue guided from the living tissue guiding groove to the proximal end part of the slit groove, and
the second electrode is arranged on a second surface of the tissue holding part opposite to the first surface on which the first electrode is arranged so as to be spaced apart from the part of the distal end of the first electrode positioned at the proximal end part of the slit groove via the tissue holding part, and is arranged so as to hold a part of the tissue holding part with respect to the cutter body.

10. The instrument for cutting a living tissue according to claim 9, wherein
the second electrode includes an arc-shaped part defining a substantially arc-shaped opening, and
the first electrode is arranged with respect to the second electrode such that the part of the distal end of the first electrode positioned at the proximal end part of the slit groove is arranged spaced apart from the center of the substantially arc-shaped opening on an axis substantially orthogonal to a longitudinal axis and a latitudinal axis of the cutter body via the tissue holding part, and that distances from the part of the distal end of the first electrode positioned at the proximal end part of the slit groove to each part of the periphery of the substantially arc-shaped opening of the second electrode are substantially equal.

11. The instrument for cutting a living tissue according to claim 10, wherein
the tissue holding part has a substantially cylindrically shaped part formed in a substantially cylindrical shape which has the slit groove arranged to substantially a center of the substantially cylindrically shaped part, and
a perimeter of one side of the substantially cylindrically shaped part and the periphery of the substantially arc-shaped opening of the second electrode are arranged so as to be superimposed on the axis substantially orthogonal to the longitudinal axis and latitudinal axis of the cutter body.

12. The instrument for cutting a living tissue according to claim 11, wherein the tissue holding part has a substantially rectangular-shaped part arranged to be extending from a side of the substantially cylindrically shaped part toward the distal end side of the insertion part, and the slit groove is formed from a distal end center part of the substantially rectangular-shaped part through substantially the center of the substantially cylindrically shaped part.

13. The instrument for cutting a living tissue according to claim 12, wherein the area of the second electrode is greater than the area of the part of the distal end of the first electrode positioned at the proximal end part of the slit groove.

14. The instrument for cutting a living tissue according to claim 13, wherein the tissue holding part is made of ceramics.

15. An instrument for cutting a living tissue comprising:
an insertion part configured to be inserted in a body, the insertion part comprising a channel in which an endoscope is inserted;
a holder for holding the living tissue provided at a distal end part of the insertion part; and
a cutter for cutting a target tissue provided at the distal end part of the insertion part on the substantially opposite side with respect to the holder, with the center of the insertion channel of the endoscope therebetween;
wherein the cutter comprises:
a cutter body having a living tissue guiding groove for guiding the target tissue to the distal end part of the insertion part;
a pair of electrodes provided at a distal end side of the cutter body; and
a tissue holding part made of ceramics provided between the pair of electrodes and having a slit groove connected to the proximal end of the living tissue guiding groove, and wherein the tissue holding part includes:
- a substantially rectangular-shaped part formed in a substantially rectangular shape on a distal end side of the tissue holding part; and
- a substantially cylindrically shaped part formed in a substantially cylindrical shape on a proximal end side of the tissue holding part.

16. The instrument for cutting a living tissue according to claim 15, wherein the pair of electrodes comprises:
   a first electrode for applying a high-frequency current; and
   a second electrode for returning the high-frequency current from the first electrode;
   wherein the cutter is formed in a three-layered structure at a part on the distal end side of the cutter body in which the first electrode is a lower layer, the second electrode is an upper layer, and the tissue holding part is arranged between the first electrode and the second electrode.

17. The instrument for cutting a living tissue according to claim 16, wherein the second electrode has an arc-shaped part defining a substantially arc-shaped opening.

18. The instrument for cutting a living tissue according to claim 17, wherein the tissue holding part comprises:
   a first convex part protruding from a first side surface of the substantially rectangular-shaped part;
   a second convex part protruding from a second side surface of the substantially rectangular-shaped part; and
   a third convex part protruding toward the proximal end of the tissue holding part from a side surface of the substantially cylindrically-shaped part;
   wherein the cutter body has three fitting grooves corresponding to the first, second and third convex parts of the tissue holding part; and
   wherein the tissue holding part is fit into the cutter body by fitting the first, second and third convex parts of the tissue holding part into the three fitting grooves of the cutter body.

19. The instrument for cutting a living tissue according to claim 17, wherein the slit groove is formed in the tissue holding part from the distal end central part of the substantially rectangular-shaped part through substantially the center of the substantially cylindrically shaped part in the longitudinal direction of the cutter body.

20. The instrument for cutting a living tissue according to claim 15, wherein the ceramics is zirconia.

21. The instrument for cutting a living tissue according to claim 15, wherein the ceramics is alumina.

* * * * *